United States Patent
Weggler et al.

(10) Patent No.: US 11,158,399 B2
(45) Date of Patent: Oct. 26, 2021

(54) SYSTEM, METHOD, COMPUTER PROGRAM PRODUCT AND USER INTERFACE FOR CONTROLLING, DETECTING, REGULATING AND/OR ANALYZING BIOLOGICAL, BIOCHEMICAL, CHEMICAL AND/OR PHYSICAL PROCESSES

(71) Applicant: Sartorius Stedim Biotech GmbH, Goettingen (DE)

(72) Inventors: Sophie Weggler, Goettingen (DE); Nils Goetje, Hannover (DE); Sascha Krumbein, Witzenausen (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 561 days.

(21) Appl. No.: 15/506,955

(22) PCT Filed: Jun. 30, 2015

(86) PCT No.: PCT/EP2015/001316
§ 371 (c)(1),
(2) Date: Feb. 27, 2017

(87) PCT Pub. No.: WO2016/029979
PCT Pub. Date: Mar. 3, 2016

(65) Prior Publication Data
US 2017/0277829 A1  Sep. 28, 2017

(30) Foreign Application Priority Data
Aug. 29, 2014 (EP) ..................................... 14002995

(51) Int. Cl.
G16B 45/00 (2019.01)
G16C 20/80 (2019.01)
G05B 23/02 (2006.01)

(52) U.S. Cl.
CPC .......... *G16B 45/00* (2019.02); *G05B 23/0237* (2013.01); *G16C 20/80* (2019.02)

(58) Field of Classification Search
None
See application file for complete search history.

(56) References Cited

U.S. PATENT DOCUMENTS

| | | |
|---|---|---|
| 6,546,134 B1 | 4/2003 | Shrairman et al. |
| 6,727,096 B1 | 4/2004 | Wang et al. |
| 2003/0028269 A1 | 2/2003 | Spriggs et al. |
| 2005/0197805 A1 | 9/2005 | Eryurek et al. |

FOREIGN PATENT DOCUMENTS

| | | | | |
|---|---|---|---|---|
| EP | 1 184 073 | 3/2002 | | |
| EP | 2 172 820 | 4/2010 | | |
| WO | WO-2009058392 A2 * | 5/2009 | .......... | G06T 11/206 |
| WO | 2014/006807 | 1/2014 | | |
| WO | WO-2014020327 A1 * | 2/2014 | .......... | C12M 27/02 |

OTHER PUBLICATIONS

Ellert et al. Process optimization made easy: design of experiments with multi-bioreactor system BIOSTAT Qplus Nature Methods vol. 8, p. i-ii (Year: 2011).*
Puskeileretal. Miniature bioreactors for automated high-throughput bioprocess design (HTBD): reproducibility of parallel fed-batch cultivations with *Escherichia coli* Biotechnology and Applied Biochemistry vol. 42, pp. 227-235 (Year: 2005).*
Isett et al. Twenty-Four-Well Plate Miniature Bioreactor High-Throughput System: Assessment for Microbial Cultivations Biotechnology and Bioengineering vol. 98, pp. 1017-1028 (Year: 2007).*
Moses et al. Assessment of AMBT as a model for high-throughput cell culture process development strategy Advances in Bioscience and Biotechnology vol. 3 pp. 918-927 (Year: 2012).*
International Search Report dated Aug. 17, 2015, PCT/EP2015/001316.
"Eppendorf DASGIP documentaion wizzard, software manual".
"Eppendorf DASware discover, software manual".
Eidesstattliche Versicherung von Herrn Falk Schneider.
"Interactive Pattern Search in Time Series", Paolo Buono et al., Proc. of VDA 2005.
Internetdokument: Timesearcher aufrufbar unter der internetaddress http://www.cs.umd.edu/hcil/timesearcher/.
Internetdokument: Timesearcher aufrufbar unter der internetaddress http://www.cs.umd.edu/hcil/timesearcher/docs/ts2_userManual.html#sec5.5.
Internetdokument: Timesearcher, License—Download aufrufbar unter der internetaddress http://www.cs.umd.edu/hcil/timesearcher/dist2/demos 4Gf5x/.
Opposition dated Jan. 18, 2018.

* cited by examiner

*Primary Examiner* — John S Brusca
(74) *Attorney, Agent, or Firm* — Gerald E. Hespos; Michael J. Porco; Matthew T. Hespos

(57) ABSTRACT

The invention relates to a computer system, a computer-implemented method, a computer program product and a user interface for controlling, detecting, regulating, and/or analyzing biological, biochemical, chemical and/or physical processes, comprising at least two units which are designed to receive a substance or material in order to carry out at least one biological, biochemical, chemical, and/or physical process on said substance. Each unit has at least one sensor which is designed to detect measurement data relating to the process. Additionally, the computer system comprises at least one display unit via which the measurement data of the two units is displayed in respective temporal correlations which allows information to be obtained on a relationship inherent in the displayed measurement data.

15 Claims, 11 Drawing Sheets

SYSTEM, METHOD, COMPUTER PROGRAM PRODUCT AND USER INTERFACE FOR CONTROLLING, DETECTING, REGULATING AND/OR ANALYZING BIOLOGICAL, BIOCHEMICAL, CHEMICAL AND/OR PHYSICAL PROCESSES

BACKGROUND

1. Field of the Invention

The present invention relates to a computer system, a computer-implemented method, a computer program product and a user interface for controlling, detecting, regulating and/or analyzing biological, biochemical, chemical and/or physical processes.

2. Description of the Related Art

Known systems facilitate a display of measurement data in real time, which data can be captured by means of a sensor of a unit, i.e. the measurement data which are displayed are coupled to a current process time. A display of measurement data independently of an absolute time of capture thereof is not possible. The display takes place by means of a display unit, which is coupled to a bioreactor or a filtration plant or a freezing and defrosting system. Furthermore, it is conventionally possible for parameters, which are significant for carrying out a biological, biochemical, chemical and/or physical process, to be set by means of the display unit. The parameters may be, for example, a pH value, an oxygen supply, etc. As a result, a process-specific visualization of measurement data as well as control of process parameters is made possible.

However, when biological, biochemical, chemical and/or physical processes are carried out in a unit which contains a reactor, it is of considerable importance to obtain a precise overview of important factors which influence the process as well as the effect of an alteration of these factors on the success of the process. For this reason it is necessary for a flow of measurement data, for example within one or more batch phases or batches of different processes, of different process configurations and/or of processes of the same and/or different configurations, which have been started at different absolute times, to be compared with one another. Conventional systems do not make it possible to present such a measurement data flow in a temporal correlation in such a way as to enable information to be obtained about a relationship inherent in the detected measurement data.

Accordingly, the object of the present invention is to be able to record and further process measurement data of biological, biochemical, chemical and/or physical processes in an improved manner.

SUMMARY

According to a first aspect of the invention the computer system for controlling, detecting, regulating and/or analyzing biological, biochemical, chemical and/or physical processes is provided, comprising
at least two entities or units, which are designed to receive a substance or a material in order to carry out at least one biological, biochemical, chemical and/or physical process on said substance;
wherein each of the units has at least one sensor which is configured to detect measurement data relating to the process; and
at least one display unit, by means of which the measurement data of the two units is displayed in respective temporal correlations which allows information to be obtained on a relationship between the presented measurement data.

A reactor may for example be a bioreactor and/or a chemical reactor which is configured to receive a substance or a material on which at least one biological, biochemical, chemical and/or physical process can be carried out. In the bioreactors both single-use reactors in the form of bags or free-standing devices as well as solid containers made of stainless steel can be used. Depending upon the type of cultivation, the bioreactors are packed with solid materials for establishment of adherent cells or are configured as stirred reactors.

Alternatively or in addition to the reactor, a unit can in particular include at least one filter which can be used for filtration of a medium. For example, this may be a filter for cross-flow filtration, which can be used for example for purification and/or separation of proteins or protein constituents; a filter for carrying out a membrane chromatography, for example for separation of cell constituents, nucleic acids, viruses, mycoplasma or endotoxins; a clarification filter, for example for purification of serum solution or plasma solution; a virus filter, for example for separation of viruses and/or virus constituents; a UV-C inactivation system, for example for separation of viruses and/or virus constituents; and/or a tangential flow filter or transverse flow filter for filtration of liquids, for example in the food and/or pharmaceutical industry.

As an alternative or in addition to the reactor or filter, a unit can in particular contain at least one freezing and thawing system, which is configured, for example, to freeze and to thaw bio-pharmaceutical liquids reproducibly in a production and process development.

The substance may be a liquid, a gas and/or a solid. The substance may be composed of at least one component which is required in order to enable the process to be carried out. Thus, for example, for cultivation of microorganisms it is necessary to create and to maintain essential conditions which ensure optimum growth of organisms. For example, such important conditions may be a combination of a nutrient medium or a nutrient solution, an oxygen content, a pH value and/or a temperature in the bioreactor. The purpose of the cultivation may ultimately be to obtain the organisms or parts of the organisms and/or the secreted or unsecreted metabolic products, which can be used as an active substance in the pharmaceutical industry or as a basic chemical in the chemical industry. Furthermore, the purpose of the cultivation may be to break down chemical compositions, for example in sewage treatment works or for fermentation of foodstuffs.

In this case each unit may be made up individually of at least one reactor, at least one sensor as well as optionally one or more individual control units and process devices, which together from a logical viewpoint constitute a part of a plant in which one or more process activities can be carried out. Each unit always generates only one batch in a given time period during a process. Thus with each unit a specific process can be presented, so that all measurement data required for process recording or process monitoring can be detected and simultaneously displayed with the aid of the sensor.

Measurement data of the substances present in the unit and/or processes proceeding therein, which can be detected, displayed and possibly correlated with measurement data of other units by the computer system, are not subject to particular limitations and are largely dependent upon the respective application and the purpose or objective thereof. The data may relate, for example, to cell density, growth rate of the cells, quantity of a culture medium, foam generation of the culture medium, pH value of the culture medium, temperature of the culture medium, oxygen content of the culture medium, carbon dioxide content of the culture medium, clouding of the culture medium, capacitance and/or conductivity of the culture medium, concentration of specific contents or nutrients of the culture medium, concentration of produced and secreted metabolic products, peptides and/or proteins in the culture medium, flow rates in specific parts of the bioreactor, or operating parameters of the bioreactor. Corresponding sensors for detection of such or other measurement data are not subject to any particular limitations and are known in the prior art. Measurement data can be detected in a specific time interval. The time interval preferably lies in a range between approximately 500 and approximately 60,000 ms. The measurement data may preferably be retrieved from each unit by the sensor (polling).

In the example of a fermentation to be carried out, a unit can be made up of a container (for example a bioreactor, a filtration plant or a freezing and thawing system), a sensor (for example a gas analysis device for analyzing O2 and/or CO2) and a further individual control unit (for example, a scale). Each of these components can be coupled to the unit by means of a corresponding device. Each device can be a communications interface or an input/output interface or a communication interface. The separation between units and devices can be achieved efficiently and simply and has the advantage that a configuration of a unit, which may be made up of at least one reactor, at least one sensor as well as the most varied individual control units, which in a simple and efficient manner can be connected with the aid of the devices to a unit, for example by means of a network. Moreover, a clear distinction is possible between the communication viewpoint, the technical viewpoint and the process viewpoint. Thus in the preceding example the gas analysis device can be coupled to the unit by means of a universal serial bus (USB) connection, wherein a sensor device serves as a communications interface. The bioreactor can, for example, exchange data with the unit via Ethernet, wherein a reactor device can serve as communications interface. A scale can be coupled to the unit by means of an individual control unit device. Required internal individual control units can be optionally coupled to the unit. For example, a calculation module can be employed which instead of a device carries out cyclical calculations and thus, in a similar manner to a device, cyclically supplies the result as a value to a control module. A sample data management module can enable the manual input of gathered sample data which had only been determined from a sample in the laboratory. This logical combination of the respective components to form a unit has the advantage that a separation between the device communication (devices) and the monitoring, that is to say a process level (units), is achieved.

Each unit has at least one sensor which is designed to detect specific, i.e. predetermined or predeterminable measurement data relating to the process. In this case, for example, the sensor may be a gas sensor, for example an O2 or CO2 oxygen sensor, a pH sensor, a glucose sensor, a lactate sensor as well as any other sensor which is designed to detect a suitable measurement variable with regard to the process to be carried out, or it may also be any combination of the sensors. Optionally each unit can additionally have at least one individual control unit. The same applies to filtration plants. The separating unit/device serves for the modular setup with which each user can configure its own process in a standardized manner without engineering.

The measurement data can be displayed via the display unit, for example in the form of measurement curves. As an alternative to this or in addition the measurement data can be displayed in the form of one or more diagrams, for example pie charts, line diagrams, bar charts, organization charts, Gantt charts, flow charts, cause-and-effect diagrams, block diagrams etc. The measurement data may be, for example, of the float, integer, double, string or Boolean type.

The measurement data can be stored in a database which is suitable for output of the stored measurement data at high speed and in short time intervals to a corresponding database access. For example, an efficient data compression can be implemented in the database.

For example, a measurement data item can be composed of the following variables:

MappingShortID→Identification of control module variables;

Timestamp→time stamp: When was the measurement data item received in the unit?;

Value→measured value of the measurement data item;

Quality→binary value, for example 0 for "good," 1 for "bad;" the quality can be determinative for whether the measurement data item is displayed by means of the display unit;

Checksum→Is generated by the computer system generated, in order to prevent data manipulation; this has the advantage that the security in the computer system is increased.

In order to optimize the process of cultivation of the cells, it is essential to obtain a precise overview of important factors of the process, on the one hand, for example an oxygen content, as well as an effect of a change of these factors on the success of the process, on the other hand, for example an effect on the cell growth by an oxygen supply or by an addition of a new nutrient medium. This can be achieved in an efficient manner, for example in the case of two processes running at the same time in different units, by display of measurement data of the sensors of the two units in respective temporal correlations which enables information to be obtained on a relationship inherent in the displayed measurement data.

In particular, this has the advantage that effects of different important process factors or a change to one or more such process factors can be detected in real time in a simple and efficient manner. Thus a continuous optimization or improvement of the process workflows is made possible. In particular, an improved, continuous user/machine interaction is achieved thereby, since a setting of biological, chemical, biochemical and/or physical process parameters can be adjusted while processes are running in the units. This can take place in particular as a function of an input from a user and/or automatically by an automatic recognition of the temporal correlation of the measurement data. As a result, a coordination or harmonization of the technical operations in the respective units is made possible.

Furthermore, a display of different technical states prevailing in the respective units is made possible by means of the display unit.

In particular, an alert can be displayed by means of the display unit if the conditions which are important for the respective biological, biochemical, chemical and/or physical process are exceeded or undershot, for example if the oxygen content of the material located in the reactor is too low or too high.

Moreover, a technical control of the respective units is made possible, as setting of parameters which are essential for the respective process is made possible during the respective process workflows in real time.

A further advantage is that by means of the temporal correlation relevant technical relationships of the processes can be made accessible independently of an absolute time of the detected measurement data by means of the output unit. Furthermore, the temporal correlation can be maintained over the duration of the different processes and can be displayed by means of the display unit.

Thus a user is enabled to manage the technical tasks of monitoring of technical parameters, controlling the technical process parameters, detecting technical relationships inherent in the various processes as well as monitoring the effects of various technical parameters on a process workflow, more efficiently and more quickly.

Furthermore, the computer system preferably comprises a detection unit, which is designed
- to recognize the temporal correlation by comparing a flow of measurement data of the respective units with one another; and
- to enable a display of corresponding measurement data of the respective units independently of an absolute time of capture thereof by means of the display unit.

In order to recognize the temporal correlation, the detection unit can first of all combine the two units into one group (unit grouping). In this case it is irrelevant whether the units are of the same type or comprise the same sensors or individual control units. Thus the system enables a free unit grouping, of which the detection unit can recognize the temporal correlation.

A temporal correlation of the measurement data can be recognized in any way, substantially as a function of the respective application and the aim or objective thereof. For example, measurement data of different units
- exceeds or undershoots one or more specific, i.e. predetermined or predeterminable, absolute values or threshold values and/or one or more relative values, for example a pH value, a $CO_2$ value or an $O_2$ value;
- corresponds to a measured highest or lowest level;
- corresponds to a specific, i.e. predetermined or predeterminable, increase of a curve which, for example, may represent a growth rate;
- corresponds to a specific, i.e. predetermined or predeterminable, decrease of a curve which, for example, may represent a death rate;
- corresponds to a specific, i.e. predetermined or predeterminable, correlation between individual variables of the measurement data after performance of a descriptive univariate data analysis (for example an examination of a distribution, a calculation of distribution parameters, a graphical data analysis or a correlation analysis);
- has a specific, i.e. predetermined or predeterminable, data density after performance of a principal component analysis (PCA);
- has specific, i.e. predetermined or predeterminable, structures or categories within the data after performance of a partial least squares regression (PLS) and/or a discriminant analysis and/or cluster analysis; and/or
- has specific, i.e. predetermined or predeterminable, structures in the data after performance of a method of advanced multivariate data analysis (for example multiway principal component analysis).

In other words, as a measurement variable, with the aid of which the measurement data of two or a more units can be temporally correlated with one another (designated hereafter as "correlation features"), progresses over time, features are dependent upon the respective application and the function or objective thereof. Such correlation features may be one or more of the following: the reaching, exceeding or undershooting a selected limit value, a suddenly increase or sudden decrease of the measurement data, a brief and temporary increase or decrease (peak) of the measurement data or reaching a predetermined gradient value of the measurement data. Example are undershooting or exceeding specific temperatures or pH values of the culture medium, reaching a required cell density, reaching a required growth rate, undershooting or exceeding limiting values of the oxygen and/or carbon dioxide content of the culture medium or reaching a required concentration of produced metabolic products in the culture medium.

The temporal correlation of the measurement data has the advantage that measurement data of the respective units, which in particular after an automatic comparison satisfy a specific, i.e. predetermined or predeterminable, condition, can be displayed automatically by means of the display unit independently of an absolute time of detection thereof, so that it is possible to obtain information on a relationship inherent in this data.

The temporal correlation can preferably be displayed, as a time window of specific, i.e. predetermined or predeterminable, size is applied to the measurement data of the respective units in such a way that measurement data located in the time window are displayed with temporal correlation independently of an absolute time of detection thereof.

In particular, the time window can be applied to the measurement data, wherein the display unit has a zoombar on which a zoom control is provided. A user can move a time window of the size N over the measurement data of the batch with the aid of a suitable input device, for example a computer keyboard, a computer mouse, a touch screen input etc., by moving the zoom control over the zoombar. The time window used in this way is also referred to hereafter as the thumb. The time window of the size N is displayed in detail in the display area in addition to the zoombar display. Consequently, the respective measurement data, which has been zoomed with the zoombar, is displayed in the form of a time window (trend).

For example, the measurement data detected by the at least one sensor can be combined as a compilation of data or data sets. For example, each batch can contain all measurement data, from filling of a unit, for example of a bioreactor or a filtration plant, to complete emptying of this unit, which is detected after a specific, i.e. predetermined or predeterminable, time period, for example a reaction time, a growth time or after a filtering process. The data can be displayed over time in the order in which it is successively collected. Data which can be determined after the end of the respective process as a result of evaluation of the substance, for example after centrifugation of the substance, (offline data) can optionally be added to the measurement data at an appropriate later time. In particular, the measurement data stored in the batch, also referred to hereafter as batch data, can be used for certification of the respective process and thus meet corresponding standards for process production.

Since above a specified density of data it is not possible for all data combined in a batch to be displayed simultaneously, by means of the computer system a default can be set, according to which the display unit always displays the last N data or data sets which have been detected and added to the batch, wherein N defines a specific, i.e. predetermined or predeterminable, number of data or data sets. This is solved with adjustable time periods. The display of all measurement data, independently of the set time period, can as a result be made possible by storing a MinMax bar for this time period.

The temporal correlation can be displayed, as a time window of specific, i.e. predetermined or predeterminable, size is applied to the measurement data of the respective units in such a way that measurement data located in the time window are displayed with temporal correlation independently of an absolute time of detection thereof. In this case this temporal correlation or synchronization of the measurement data can be retained in the display unit, even if new measurement data is incorporated in the batch. In other words, the display unit can retain and display only the temporally correlated data located within the time window during two currently running processes. For example, measurement data, which has been detected by the sensors of the two units and which after an automatic comparison of the measurement data satisfy a specific, i.e. predetermined or predeterminable, condition, independently of the absolute time of detection thereof can be displayed via the time window with temporal correlation by means of the display unit during further running of the processes In this case the new data or data sets, which are detected by the sensors and are added to the corresponding batch, are not displayed by the display unit.

In another example, the temporal correlation can be set, as measurement data which have been measured by sensors of the respective units at different time intervals, are brought into temporal correlation with one another. In particular, the size of the time window which is adapted to the respective batch can be adapted in such a way that the measurement data correspond to one another in their time intervals.

The temporal correlation is preferably set as a function of a user input.

For example, by means of the zoombar on which a zoom control is provided, a user can move an area of the measurement data displayed via the display unit with the aid of a suitable input device, for example a computer keyboard, a computer mouse, a touch screen input, etc., by moving the zoom control.

This has the advantage that an improved continuous user/machine interaction is achieved, since the user can control the display of the measurement data of the respective units by means of a progression over time with the aid of the display unit control, and can display the measurement data with time correlation.

Moreover, it is possible for the user to set a width of the thumb and thus a number of measurement data to be displayed, by selecting a point on the zoombar which is located outside the thumb with the aid of a suitable input device, for example a computer keyboard, a computer mouse, a touch screen input etc. Thus the end of the thumb located on the side of the selected point is expanded towards the point.

In particular, with the aid of a suitable input device the user can increase or decrease the width of the thumb as well as moving the thumb arbitrarily to the right and left within the zoombar. This has the advantage that the display of the technical states of the individual units as well as the display of relevant technical relationships independently of the absolute time of detection of the measured values can be controlled while the processes are running in the units.

The measurement data of the two units is preferably displayed by means of the display unit in respective display areas, wherein, during the setting, in each display area the user applies a respective time window at specific, i.e. predetermined or predeterminable, times to the measurement data with the aid of a zoom control, which adjusts the time window or thumb for the measured values to be displayed and which can be moved along the measurement data in the respective display area.

For example, with the aid of the zoom control a user can manually cause display of measurement data which provides information on a temperature during the process of cultivating yeast cells in pure culture, wherein the process is still running and thus new measurement data is always stored in the batch. If the user finds a relevant temperature value, the user can cause display of the measurement curve from this relevant temperature value onwards, in order to monitor the further temperature profile from the relevant time onwards namely independently of the absolute time of detection of the measured values.

For example, the measurement data of each unit can be combined in a dedicated batch. Accordingly, the measurement data of each unit can be displayed in a respective specific, i.e. predetermined or predeterminable, area of the display unit, hereafter also referred to as a display area. In this example a respective zoombar can be provided for each display unit.

For example, one zoombar can correspond to each display area. Thus by moving a respective zoombar a user can select particular measurement data for display by moving a respective zoom control.

This has the advantage that over a specific, i.e. predetermined or predeterminable, period of time a user can control measurement data of each of the two units individually and independently of one another and/or can have the measurement data displayed by means of the display unit. A further advantage is that by means of the temporal correlation relevant technical relationships of the processes can be made accessible independently of an absolute time of the detected measurement data by means of the output unit. Moreover, with the aid of the time window or thumb the temporal correlation of the technical relationships is maintained over the duration of the different processes.

The computer system preferably additionally comprises a control module which is designed to combine at least two units into a group. The group can be controlled by means of the control module. Furthermore, regulation of the measurement data can be carried out by means of the control module.

For example, the control module can link the time windows to one another or place them in a ratio to one another or connect them in such a way that temporally correlated measurement data of the respective units can be displayed automatically by means of the display unit independently of an absolute time of detection thereof. For this purpose, the zoombar can be moved automatically onto the areas of the respective batches at which the measurement data satisfy the condition.

The measurement data flow of a process is also referred to below as a trend. During a synchronization of the trend a breadth of a trend can be adapted by means of a first zoombar representing N measurement data of a batch to a breadth of a second trend by means of a second zoombar representing more or less than N measurement data of a batch, so that within the trend the same time period, i.e. the same number of measurement data, is displayed.

This has the advantage that a synchronous display of different important process factors or a change to one or more such process factors can be controlled in real time in a simple and efficient manner.

Moreover, the control module is designed to link temporally correlated time windows of the respective units to one another in such a way that a user can control the plurality of time windows with the aid of a single zoom control, by moving only a respective one-time window with the aid of the zoom control by means of the zoom bar. For example, each action which is produced automatically or by a user by means of a first zoombar (actuator) is reflected in the second zoombar (reactor). In the case where the performed action in the reactor cannot be applied completely, but only partially, the action in the reactor can be performed correspondingly partially. In the case where the action cannot be performed in the reactor, the action can be reversed in the reactor.

An action can be performed, for example, only partially if a widening of a thumb is initiated towards the left in an actuator, which in principle is also possible on the reactor, albeit not to the initiated extent. In this case the initiated action of widening the thumb is performed only as far as the area which is possible for the reactor (and thus by definition for the actuator). If a widening of the thumb is impossible in the reactor, the action is not performed.

The linking of the time windows has the technical advantage of an improved control of the respective process parameters. Moreover, relevant technical relationships of different processes are made available to the user independently of an absolutely detection of corresponding measured values, which leads to the technical advantage of an improved analysis of the respective technical process parameters.

Moreover, the control module is preferably designed so that, at the same time and independently of the absolute time, it starts processes which are to be carried out on the substances of the respective units.

This can either take place automatically, by predetermining a time for the start, or manually by a suitable user input.

The substance is preferably a composition consisting of liquid and gaseous fluids, for example a gassed aqueous solution of nutrients, to which is added the microorganisms to be cultivated. In addition, for example for cultivation of adherent cells, the composition can contain solids onto which the cells can settle. However, the substance may also be of a purely chemical nature containing no microorganisms.

According to a further aspect of the present invention, the object of the invention is achieved by a computer-implemented method for controlling, detecting, regulating and/or analyzing biological, biochemical, chemical and/or physical processes, wherein the method contains the following functions:
provision of at least two entities or units, which are designed to receive a substance or a material in order to carry out at least one biological, biochemical, chemical and/or physical process on said substance, wherein each of the units has at least one sensor;
detection by the sensors of measurement data relating to the respective process; and
display by a display unit of the measurement data of the two units in a temporal correlation;
wherein the temporal correlation allows information to be obtained on a relationship inherent in the displayed measurement data.

Thus a user is enabled to manage the technical tasks of monitoring the technical parameters, control of the technical process parameters, detection of technical relationships inherent in the respective processes as well as monitoring of the effects of various technical process parameters on a process workflow, more efficiently and more quickly.

Moreover, the method preferably contains the following functions:
recognition by a detection unit of the temporal correlation, by comparison of a run of measurement data of the respective units with one another; and
display by the display unit of corresponding measurement data of the respective units independently of an absolute time of capture thereof.

The temporal correlation can preferably be displayed, as a time window of specific, i.e. predetermined or predeterminable, size is applied to the measurement data of the respective units in such a way that measurement data located in the time window are displayed with temporal correlation independently of an absolute time of detection thereof.

The temporal correlation is preferably set as a function of a user input.

The measurement data of the two units can preferably be displayed by means of the display unit in respective display areas.

Preferably, moreover, during the setting, in each display area the user applies a respective time window at a specific, i.e. predetermined or predeterminable, time to the measurement data with the aid of a zoom control, which can be moved along the measurement data in the respective display area.

The method preferably additionally contains the following function:
combination, by means of a control module, of at least two units to form a group, so that the group can be controlled by means of the control module. Furthermore, regulation of the measurement data can be carried out by means of the control module.

The method preferably additionally contains the following function:
linking of time windows, by means of the control module, which are used by means of measurement data of the respective units and are displayed respectively in a display area, so that a user can control the time windows with the aid of a zoom control by moving the time windows synchronously over the measurement data of the respective units.

The method preferably additionally contains the following function:
starting, by means of the control module, at the same time and independently of the absolute time, of the processes which are to be carried out on the substances of the respective units.

According to a further aspect of the present invention, the object of the invention is achieved by a computer program product which comprises program parts which, when loaded in a computer, are suitable for carrying out a computer-implemented method, wherein the computer-implemented method comprises the following functions:
recognition by a detection unit of a temporal correlation, by comparison of a run of measurement data of the respective units with one another; and
display by the display unit of corresponding measurement data, in a temporally corresponding manner, independently of an absolute time of capture thereof.

The temporal correlation can preferably be displayed, as a time window of specific, i.e. predetermined or predeterminable, size is applied to the measurement data of the respective units in such a way that measurement data located in the time window are displayed with temporal correlation independently of an absolute time of detection thereof.

The temporal correlation can preferably be set manually by a user.

The measurement data of the two units can preferably be displayed by means of the display unit in respective display areas.

Preferably, moreover, during the manual setting, in each display area the user applies a respective time window at a specific, i.e. predetermined or predeterminable, time to the measurement data with the aid of a zoom control, which can be moved along the measurement data in the respective display area.

The method preferably additionally contains the following function:
combination, by means of a control module, of at least two units to form a group, so that the group is controlled by means of the control module.

The method preferably additionally contains the following function:
linking of time windows, by means of the control module, which are used by means of measurement data of the respective units and are displayed respectively in a display area, so that a user can control the time windows with the aid of a zoom control by moving the time windows synchronously over the measurement data of the respective units.

The method preferably additionally contains the following function:
starting, by means of the control module, at the same time, of the processes which are to be carried out on the substances of the respective units.

According to a further aspect of the present invention, the object of the present invention is achieved by a graphical user interface (GUI) for controlling, detecting, regulating and/or analyzing biological, biochemical, chemical and/or physical processes, wherein the GUI comprises:
at least two display areas of a specific, i.e. predetermined or predeterminable, size and a specific, i.e. predetermined or predeterminable, position, wherein each display area is associated with one unit which is designed to receive a substance or a material in order to carry out at least one biological, biochemical, chemical and/or physical process on said substance,
wherein each of the units has at least one sensor which is designed to detect measurement data relating to the process, and
wherein in each display area the measurement data of the two units is displayed in respective temporal correlations which allows information to be obtained on a relationship between the presented measurement data.

Preferred embodiments are described by way of example below with reference to accompanying drawings. It will be noted that even if embodiments are described separately, individual features thereof may be combined to produce additional embodiments.

DETAILED DESCRIPTION

Figure 1:
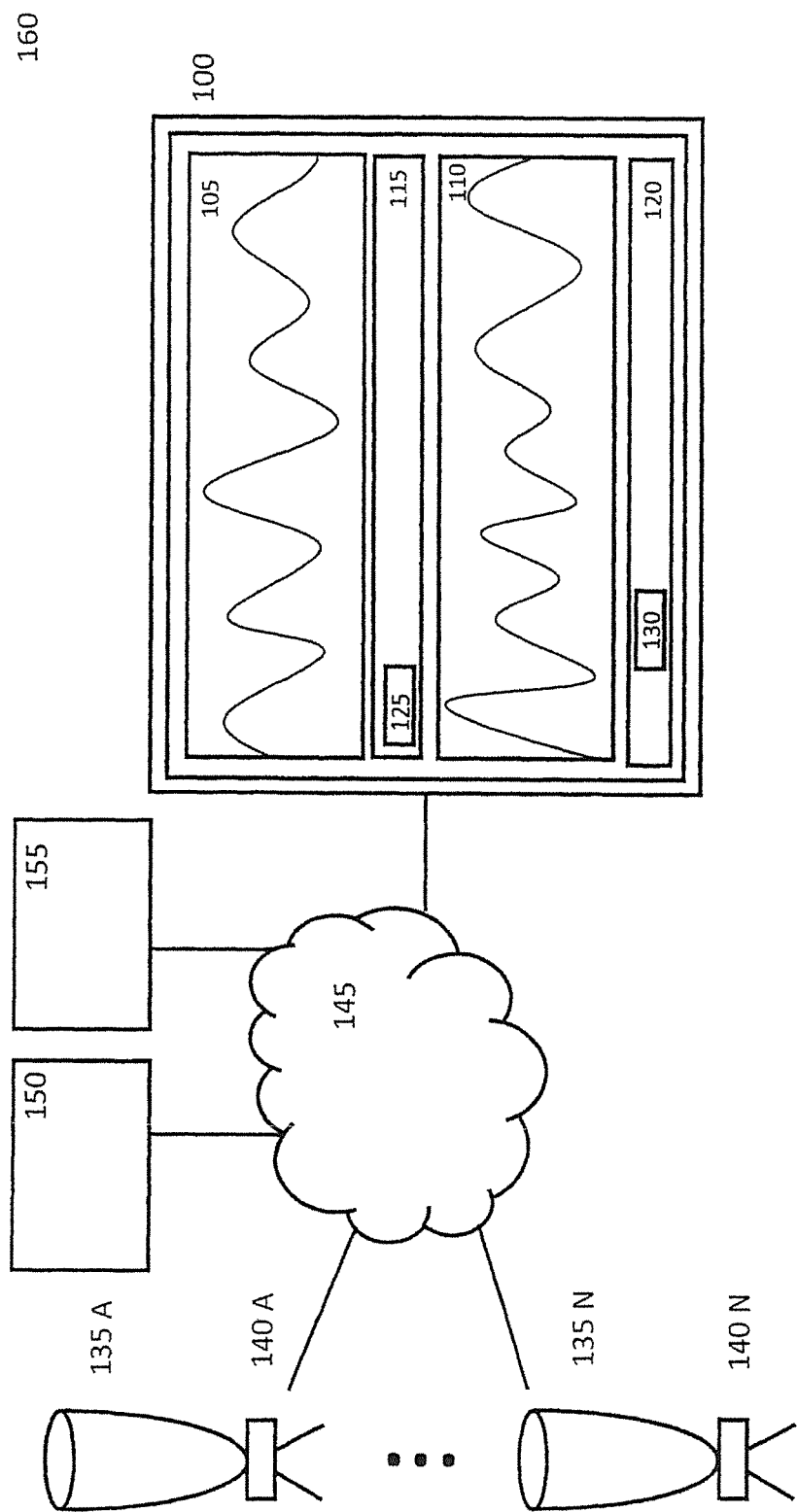
FIG. 1 shows an example of a computer system for controlling, detecting, regulating and/or analyzing biological, biochemical, chemical and/or physical processes.

FIG. 1 shows a computer system 160 for controlling, detecting, regulating and/or analyzing biological, biochemical, chemical and/or physical processes. The computer system 160 shown in FIG. 1 comprises a plurality of, but at least two units 135 A to 135 N (135 A-N), which are designed to receive a substance or a material in order to carry out at least one biological, biochemical, chemical and/or physical process on said substance. Each of the units 135 A-N has at least one sensor 140 A to 140N (140 A-N) which is configured to detect measurement data relating to the process; and Moreover, the computer system 160 comprises at least one display unit 100 via which the measurement data of the units 135 is displayed in respective temporal correlations which allows information to be obtained on a relationship inherent in the displayed measurement data. For example, the measurement data of the respective units 135 A-N can be displayed in dedicated display areas 105, 110. Moreover, by means of the display unit 100 with the aid of a respective zoom control 125, 130 the user can apply a time window by means of the corresponding zoombars 125, 130 to the measurement data of the respective batches, so that the flow of the measurement data coming from the respective time window, independently of an absolute time of the measurement data, is output by means of the display unit 100.

In particular, the computer system 160 for controlling, detecting, regulating and/or analyzing biological, biochemical, chemical and/or physical processes can be designed as a Supervisory Control and Data Acquisition (SCADA) system. Consequently, a technical process can be monitored, controlled and/or regulated by computer.

In SCADA systems, in particular, automations corresponding to the Open System Interconnection (OSI) layer model can be divided into a plurality of layers, wherein the OSI layer model in particular represents a reference model for manufacturer-independent communication systems or a design basis for communication protocols and computer networks, which meets an ISO standard. The OSI layer model consists of 7 layers:

Layer 7: Application: Functions for applications, as well as the data input and output.
Layer 6: Presentation: Conversion of the system-independent data into an independent format.
Layer 5: Communication: Controlling the connections and the data exchange.
Layer 4: Transport: Association of the data packets with an application.
Layer 3: Network: Routing the data packets to the next node.
Layer 2: Security: Segmentation of the packets in frames and addition of checksums.
Layer 1: Bit transmission: Conversion of the bits into a signal appropriate for the medium and physical transmission.

Each layer has to perform a specific function within the communication between two systems. For each layer functions and protocols are defined which have to perform specific tasks in the communication between two systems. In the communication between two systems the communication or the data flow runs through in particular all 7 layers of the OSI layer model twice. Once in the transmitter and once in the receiver. Depending upon how many intermediate stations the communication route includes, the communication also runs through the layer model several times. In this connection, protocols are a collection of rules for communication on a specific layer of the OSI model. The terminal devices of the end systems and the transmission medium are excluded from the OSI model. However, the terminal devices in the application layer and the transmission medium in the bit transmission layer can be predetermined. The protocols of one layer are in particular as transparent as possible to the protocols of the layers above and below them, so that the behavior pattern of a protocol is presented as in the case of a direct communication with the counterpart on the opposite side. The transitions between the layers may in particular be interfaces, which must be understood by the protocols. Because some protocols have been developed for quite specific applications, it also happens that protocols extend over a plurality of layers extend and cover a plurality of tasks. It may even be that in some connections individual tasks are carried out a number of times.

The term SCADA usually relates to centralized/decentralized systems which monitor, visualize and/or control or regulate entire installations. The majority of the regulation is carried out automatically by remote terminal units (RTU) or by programmable logic controllers (referred to as PLC) or Level 1 automations. The objective of the Level 2 automation is to optimize the function of Level 1 automation and also to output manipulated variables and target values. On the other hand, the Level 3 automation serves for planning, quality assurance and/or documentation.

The communication within a SCADA system can take place on the basis of TCP-based internet techniques, wherein one or more serial connections in the form of point-to-point communication and/or field bus systems are possible.

The data detection usually begins with Level 1 and includes the coupling to measuring devices and status information such as switch positions which are detected by the SCADA system. The data is then presented in a user-friendly display and makes it possible to intervene in the process for control purposes.

SCADA systems typically implement a distributed database which contains data points. A data point contains an input or output value which is monitored and/or controlled by the system. Data points can be physically calculated. A physical data point constitutes an input or output, whilst a calculated point is produced by mathematical operations from the status of the system. Data points are normally treated as a combination of values with time stamps. A series of data points enables the historic evaluation.

In this case the temporal correlation of data points from various units 135 A-N can be used advantageously in order to detect relationships of the corresponding data points or measurement data. This advantageously enables a user, on the basis of a display of the measurement data in a temporally correlated manner, to have a corresponding influence on the process or the processes, for example by setting corresponding process parameters, triggers of specific operations or the like.

Each temporal correlation comprises a horizontal movement or alignment of the measurement data of the respective units 135 A-N, so that the measurement data can be related to one another in any way.

One unit 135 A-N or plant unit comprises, in particular, at least one reactor, for example at least one bioreactor and/or at least one chemical reactor, at least one sensor 140 A-N as well as optionally one or more individual control units and process devices. From the logical viewpoint, each unit 135 A-N as a whole can constitute a part of a production facility, for example in a production plant for production of yeast cultures, in which one or more process activities can be carried out. Each unit 135 A-N generates from the measurement data which is detected by the sensor 140 A-N and optionally by individual control units at a given time, preferably only a batch. Each unit 135 A-N can act independently of any other unit 135 A-N. Thus with each unit 135 A-N a specific, i.e. predetermined or predeterminable process can be presented, so that all measurement data required for process recording or process monitoring can be detected and simultaneously displayed with the aid of at least one sensor 140 A-N. According to a specific process each unit 135 A-N can be assembled individually by the necessary process from any combination of the above-mentioned components.

Alternatively or in addition to the reactor, a unit 135 A-N can in particular include at least one filter which can be used for filtration of a medium. This may, for example, be a filter for cross-flow filtration or tangential-flow filtration or transverse-flow filtration, in which liquids for example for the food and/or pharmaceutical industry are filtered. In this case a suspension to be filtered at a high speed is pumped parallel to a membrane or a filter medium, wherein a solid material or permeate transversely is drawn off transversely with respect to the flow direction. The cross-flow filtration can be used, for example, in microfiltration, ultrafiltration, nanofiltration, gas separation, pervaporation and/or reverse osmosis. Each of these units 135 A-N comprises at least one sensor 140 A-N as well as optionally one or more individual control units and process devices. From the logical viewpoint, each unit 135 A-N as a whole can constitute a part of a production facility, for example in a water treatment works for removing heavy metals in the water treatment, in which one or more process activities can be carried out. Each unit 135 A-N generates from the measurement data which is detected by the sensor 140 A-N and optionally by the individual control units at a given time, preferably only a batch. Each unit 135 A-N can act independently of any other unit 135 A-N. Thus with each unit 135 A-N a specific process can be presented, so that all measurement data required for process recording or process monitoring can be detected and simultaneously displayed with the aid of at least one sensor 140 A-N. According to a specific process each unit 135 A-N can be assembled individually by the necessary process from any combination of the above-mentioned components.

A sensor 140 A-N is in particular a technical component which can quantitatively detect specific biological, biochemical, chemical and/or physical properties of its environment as a measurement variable. In this case the biological, biochemical, chemical and/or physical properties are converted into an electrical and/or optical signal. The electrical signal can then be scanned. In this case a digital measurement data item or a digitally measured value can be generated for each biological, biochemical, chemical and/or physical characteristic. Thus the sensor 140 A-N can produce a data stream of the corresponding measurement data.

Each unit 135 A-N has in particular at least one sensor 140 A-N which is designed to detect specific, i.e. predetermined or predeterminable measurement data relating to the process. In this case, for example, the sensor may be a gas sensor, for example an O2 or CO2 sensor, a pH sensor, a glucose sensor, a lactate sensor and/or any combination of sensors which are designed to detect a suitable measurement variable with regard to the process to be carried out. Moreover, each unit 135 A-N may optionally have one or more individual control units.

A bioreactor or fermenter 225 as a specific embodiment of a unit 135 A-N (as described below with respect to FIG. 2) is in particular a container designed to cultivate or to ferment cells, microorganisms and/or small plants. In the bioreactor 225 biological processes, for example a bioconversion or a biocatalysis, can be used or can be made useful in technical devices. In this case attempts are made to achieve optimum cultivation conditions with the aid of important factors which can be controlled in the bioreactor 225. Controllable factors may be, for example, a combination of a nutrient solution or of a substrate, an oxygen supply, a sterility or a pH value. The purpose of a cultivation in the bioreactor 225 may be obtaining cells, obtaining cell constituents or obtaining metabolic products or metabolites, which can then be used, for example, as an active substance in the pharmaceutical industry or as a basic chemical in the chemical industry. Examples of such bioreactors are, for example, autoclavable bioreactors, in situ serializable bioreactors, disposable bioreactors, stirred tank reactors, fixed bed reactors or photobioreactors. Also the production of alcohol or alcoholic beverages, for example beer, can take place in bioreactors, for example a brewing kettle. In particular, bioreactors are not subject to any specific restrictions. They comprise, for example, bioreactors for culturing cells, such as bacteria, yeast, insect, plant or mammalian cells; bioreactors for producing metabolic products of such cells; bioreactors for producing peptides or proteins which are expressed by such cells; bioreactors for energy production with the aid of such cells; bioreactors for multiplying viruses with the aid of such cells; bioreactors for breaking down substances with the aid of such cells; bioreactors for producing foodstuffs with the aid of such cells; bioreactors for generating biogas with the aid of such cells; and combinations thereof.

An individual control unit 230 (as described below with respect to FIG. 2) is a technical component, which may be a sensor 140 A-N, n actuator, a pump, a counter or a totalizer as well as any suitable processing device. In particular, an individual control unit 230 may also be any combination of the above-mentioned technical components, also referred to as a control module, which can act as one unit, such as for example a circulation pump, a servo, a control device or a pneumatic cylinder with feedback message to a control unit. Moreover, an individual control unit 230 can be made up of a plurality of individual controller units, for example a main control module consisting of a combination of a plurality of automatic in/out valve control modules or on/off automatic block valves. Thus individual control unit2 230 may, for example, be
- a regulation device, which is made up of a transmission unit or a transmitter, a regulating unit or a controller and a regulator valve or a control valve;
- a condition-oriented device, which comprises an automatic in/out valve control module with position feedback switch, which can be operated and/or controlled by means of a theoretical value of the device; or
- a header, which includes a plurality of automatic in/out valve control modules and which coordinates the valves in such a way that a flow rate leads through the valve to one or more targets.

A control module 325 (as described below with respect to FIG. 3) comprises in particular variables which belong together as a physically measured or calculated value. The control module can also optionally control or adjust the variables. Different types of control modules can be provided: controller, process variable, digital variable and/or offline variable.

In device 205, 210, 215 (as described below with respect to FIG. 2) in particular constitutes an interface for the connection of an element to a unit. For example, a sensor device 205 can constitute an interface for the connection of an $O_2/CO_2$ analysis sensor to the unit. Furthermore, a reactor device 210 can constitute an interface for the connection of a bioreactor 225. Likewise, an individual control unit device 215 can constitute an interface for the connection of a scale to the unit.

A batch is, in particular, a compilation of data or data sets, which are detected as measurement data by the respective components of a unit within a specific, i.e. predetermined or predeterminable, time period. In particular, a batch is a recording of measurement data by means of the process, which can be carried out by the respective unit and thus can also be archived. Each batch can be stored in a database after the ending of the process. Thus it can be used repeatedly for an analysis and/or evaluation. Thus each batch repeatedly includes the characteristic process sequences which run over the same time period. The data or data sets can be stored and displayed by means of the output unit over time in the order in which it is successively collected. For example, each batch can contain all measurement data, which in the time period between a filling of a unit, for example a reactor or bioreactor, and complete emptying of this unit, which is detected after a specific, i.e. predetermined or predeterminable, time period, for example a reaction time or growth time, Measurement data or process data is in particular data or data sets which contain information about a value of a property at a given time. Measurement data can be stored in a database.

A substance may, in particular, be a liquid, a gas and/or a solid. The substance may be composed of at least one component which is required in order to enable the process to be carried out. Thus, for example, for cultivation of specific organisms, for example cells or specific parts of organisms, it may be necessary to create and to maintain important conditions which ensure optimum growth of organisms. For example, such important conditions may be a combination of a nutrient medium or a nutrient solution, or of a substrate, a pH value and/or a sterility in the bioreactor. The purpose of the cultivation may be collection of organisms, for example cells and parts of organisms. A further purpose of the cultivation may be to obtain metabolic products, which can be used as an active substance in the pharmaceutical industry and/or as a basic chemical in the chemical industry. Furthermore, the purpose may be to break down chemical compositions, for example in sewage treatment works, or to produce alcoholic beverages.

The measurement data 335 (see below with reference to FIG. 3) can be displayed via the display unit 100, for example in the form of measurement curves. As an alternative to this and/or in addition the measurement data can be displayed in the form of one or more diagrams, for example pie charts, line diagrams, bar charts, organization charts, Gantt charts, flow charts, cause-and-effect diagrams and/or block diagrams.

In order to enable optimization of processes, for example a cell cultivation, it is necessary to have a precise overview of important factors of the process, for example an oxygen content. Furthermore, it is important to obtain information about an effect of a change of these factors on the success of the process, on the other hand, for example an effect on the cell growth by an oxygen supply or by an addition of a new nutrient medium. This can be achieved in an efficient manner, for example in the case of two processes running concurrently in different units 135 A-N, by display of measurement data of the sensors 140 A-N of the two units 135 A-N in respective temporal correlations which enables information to be obtained on a relationship inherent in the displayed measurement data. The individual components of the computer system 160 can be connected to one another via suitable network 145, for example a "local area network" (LAN) or a "wide area network" (WAN).

Optionally, the computer system 160 can comprise a detection unit 150 which is designed to recognize the temporal correlation automatically. For example, the detection unit 150 can compare a flow of the measurement data of the respective units 135 A-N with one another and can display measurement data items which correspond to one another, independently von an absolute time of detection thereof in a temporally correlated manner by means of the display unit 100 in the respective display areas 105, 110.

A temporal correlation of the measurement data can be recognized in any way, substantially as a function of the respective application and the aim or objective thereof. For example, measurement data of different units
- exceeds or undershoots one or more specific, i.e. predetermined or predeterminable, absolute values or threshold values and/or one or more relative values, for example a pH value, a $CO_2$ value or an $O_2$ value;
- corresponds to a measured highest or lowest level;
- corresponds to a specific, i.e. predetermined or predeterminable, increase of a curve which, for example, may represent a growth rate;
- corresponds to a specific, i.e. predetermined or predeterminable, decrease of a curve which, for example, may represent a death rate;
- corresponds, in particular, to an alert which can be triggered if the conditions which are important for the respective biological, biochemical, chemical and/or physical process are exceeded or undershot, for example if the oxygen content and/or pH value of the material located in the reactor is too low or too high.
- corresponds to a specific, i.e. predetermined or predeterminable, correlation between individual variables of the measurement data after performance of a descriptive univariate data analysis (for example an examination of a distribution, a calculation of distribution parameters, a graphical data analysis or a correlation analysis);
- has a specific, i.e. predetermined or predeterminable, data density after performance of a principal component analysis (PCA);
- has specific, i.e. predetermined or predeterminable, structures or categories within the data after performance of a partial least squares regression (PLS) and/or a discriminant analysis and/or cluster analysis; and/or
- has specific, i.e. predetermined or predeterminable, structures in the data after performance of a method of advanced multivariate data analysis (for example multiway principal component analysis).

Alternatively or in addition, a user can place a marker in a displayed measurement data flow with the aid of a suitable input device, such as for example a keyboard and/or a computer mouse. A temporal correlation of the measurement data can be identified on this marker.

Alternatively or in addition, each batch can be divided into different phases. For example, a first phase can correspond to an introduction of a material into a unit, a second phase corresponds to an addition of cells to the material, a third phase corresponds to an addition of further cells to the material, etc. In this case a temporal correlation of the measurement data can be identified, as measurement data of different units correspond to the beginning of a specific phase.

This has the advantage that measurement data of the respective units 135 A-N, which after an automatic comparison satisfy a specific, i.e. predetermined or predeterminable, condition, can be displayed automatically by means of the display unit 100 independently of an absolute time of detection thereof, so that it is possible to obtain information on a relationship inherent in this data.

Optionally, the computer system 160 can comprise a control module 155 which is designed to combine at least two units 135 A-N into a group, so that the group can be controlled simultaneously by means of the control module 155 (as explained below with respect to FIG. 4).

In particular, the computer system 160 has the advantage that effects of different important process factors or a change to one or more such process factors can be detected in real time in a simple and efficient manner. Thus a continuous optimization or improvement of the process workflows is made possible. In particular, an improved, continuous user/machine interaction is achieved thereby, since a setting of biological, chemical, biochemical and/or physical process parameters can be adjusted or input while processes are running in the respective units 135 A-N specifically and as a function of the corresponding state of the process. As a result, a coordination or harmonization of the technical operations in the respective units 135 A-N is made possible.

Furthermore, a display of different technical states prevailing in the respective units 135 A-N is made possible by means of the display unit 100.

In particular, an alert can be displayed by means of the display unit 100 if the conditions which are important for the respective biological, biochemical, chemical and/or physical process are exceeded or undershot, for example if the oxygen content and/or pH value of the material located in the reactor is too low or too high.

Moreover, a technical control of the respective units 135 A-N is made possible, as setting of parameters which are essential for the respective process is made possible during the respective process workflows in real time.

A further advantage is that by means of the temporal correlation relevant technical relationships of the processes in the respective units 135 A-N can be made accessible independently of an absolute time of the detected measurement data by means of the display unit 100. Furthermore, the temporal correlation can be maintained over the duration of the different processes in the respective units 135 A-N.

Thus a user is enabled to manage the technical tasks of monitoring of technical parameters, controlling the technical process parameters, detecting technical relationships inherent in the various processes as well as monitoring the effects of various technical parameters on a process workflow in the respective units 135 A-N, more efficiently and more quickly.

Figure 2:
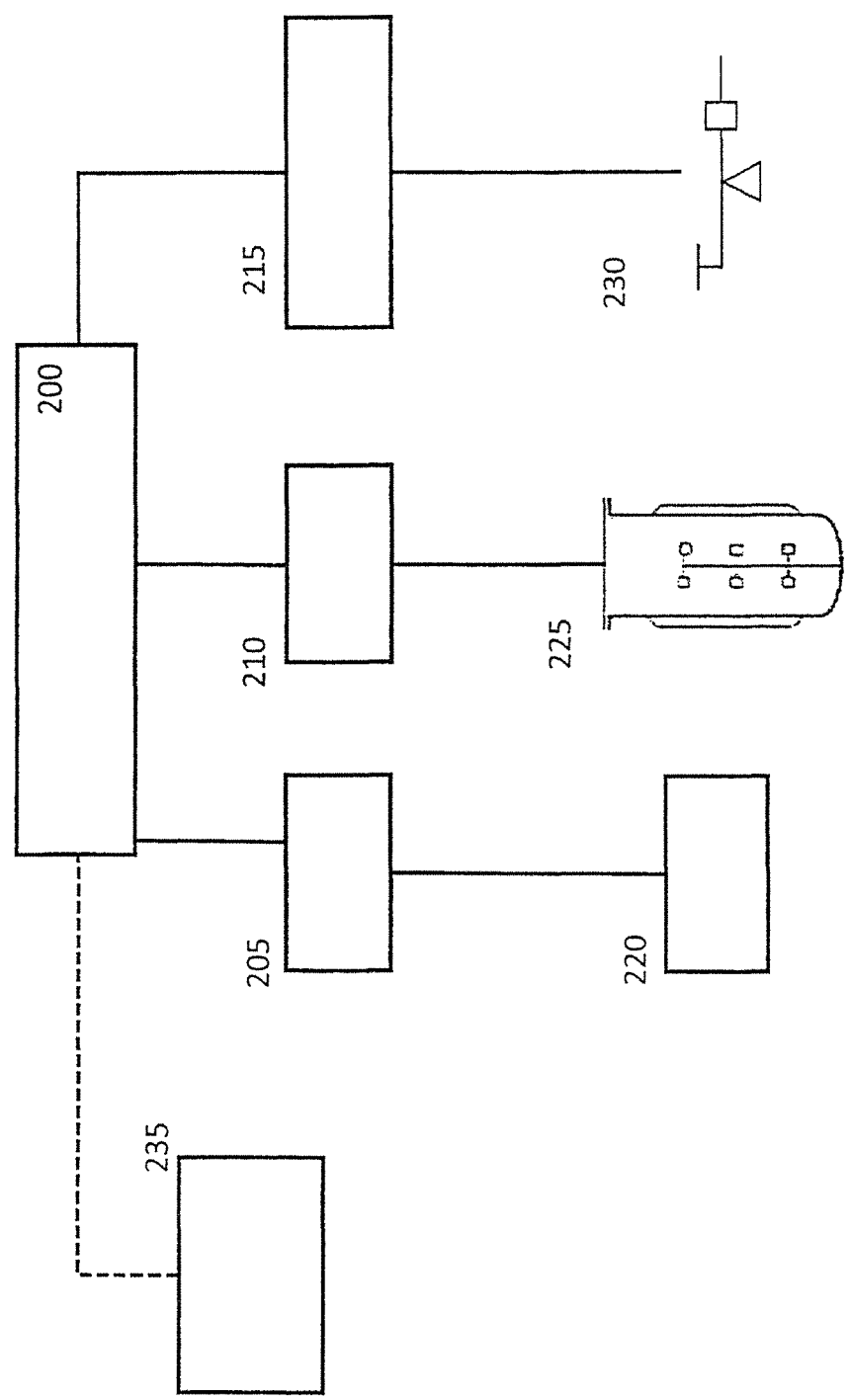
FIG. 2 shows an example of the setup of a unit.

FIG. 2 shows a block diagram of an example of a unit 200. In particular, the unit 200 comprises a reactor 225 or a filter, which is designed to receive a substance or a material in order to carry out at least one biological, biochemical, chemical and/or physical process on said substance. Moreover, the unit 200 has a sensor 220, for example an O2/CO2 analyzer which is configured to detect measurement data relating to the process. Furthermore, the unit 200 comprises an individual control unit 230, for example a scale and/or one or more internal individual control units 235. Each of the internal individual control units 235 can be configured to carry out calculations relating to the detected measurement data and/or to take and/or to analyze samples of the substance on which the process is carried out.

Each of these components can be coupled to the unit 200 by means of a corresponding device 205, 210, 215. Each device 205, 210, 215 can be a communication interface. The separation between units 200 and device 205, 210, 215 has the advantage that a configuration of a unit 200 can be carried out in a simple and efficient manner, since the respective components 220, 225, 230 can be connected to the unit 200 with the aid of the devices 205, 210, 215. In particular, the O2/CO2 gas analysis device 220 can be coupled to the unit 200 by means of a universal serial bus (USB) connection, wherein a sensor device 205 serves as a communications interface. The bioreactor 225 can, for example, send corresponding measurement data to the unit 200 and/or exchange further data with the unit 200 via Ethernet, wherein a reactor device 210 can serve as communications interface for this purpose. The scale 230 can be coupled to the unit 200 by an individual control unit device 215. Required internal individual control units 235 can be optionally coupled to the unit 200.

A control module 325 (as described below with respect to FIG. 3) can combine variables which belong together as a value which is physically measured or calculated or determined by the sensor 220. The control module 325 can also optionally control or adjust the variables. Different types of control modules 325 can be provided: Controller, process variable, digital variable and offline variable. For example, the unit 200 can include a temperature sensor for the detection of a temperature. A control module 325 corresponding to the temperature sensor can be provided. This control module 325 may be of the controller type. In the present example a control module 325 can have the following variables:

Temp.Value→actual temperature value;
Temp.Setpoint→desired temperature value;
Temp.Output→temperature output variable;
Temp.Mode→temperature mode, e.g. automatic, manual, profile, cascade;
Temp.Status→temperature status, e.g. remote, off. The status value can specify whether the value can be written. The status value constitutes a security function;
Temp.Value.EngineeringUnit→° C.;
Temp.Output.EngineeringUnit→%;
Temp.HighLimit→Specifies an upper temperature threshold value on; can output an alert if a specific, i.e. predetermined or predeterminable value is exceeded;
Temp.HighH ighLimit→Triggers an alert when an absolute temperature upper limit is exceeded;
Temp.LowLimit→Specifies a lower temperature threshold value on; can output an alert if a specific, i.e. predetermined or predeterminable value is exceeded;
Temp.LowLowLimit→Triggers an alert when an absolute temperature lower limit is undershot;
Temp.UnitID→Specifies the ID of the unit 200 on which the control module 325 is placed. Thus each control module 325 can be unambiguously assigned;

Each control module variable can be assigned its own MappingShortID. This has the advantage that the corresponding incoming measurement data can be assigned unambiguously to a control module variable.

Figure 3:
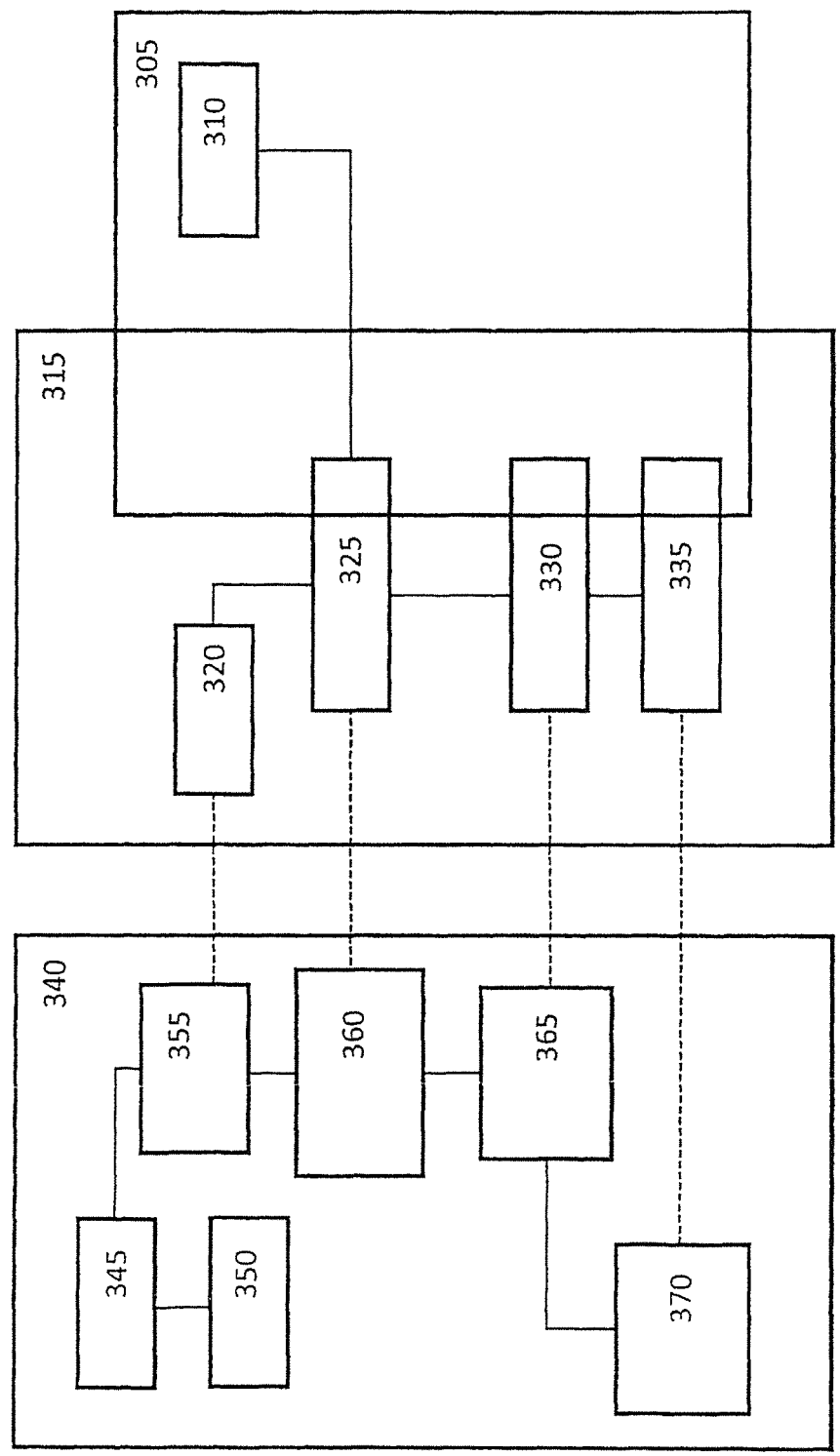
FIG. 3 shows an overview of an example of a structure and relationships of measurement data of a unit which are combined into a batch.

FIG. 3 shows an overview of an example of a structure and relationships of measurement data 335 of a unit 320 which are combined into a batch 350.

In this case from the communication viewpoint 305 communication can take place with each unit 320 via a control module 325. Each control module 325 can comprise control module variables 330. A control module can be a summary of variables and/or values which belong to a physical quantity. Every control module has at least one value (for example 34.5), an entity (for example ° C.), a unit and a "source" (a device from which the values or a calculation of the values originate). Optionally, a control module can contain additional variables (for example desired value, output variable and/or LowLimit or alert limit). Moreover, a view of the measurement data 335 is possible. From the user viewpoint 315 or monitoring viewpoint each control module 325 is assigned to a unit 320 associated and can have one or more control module variables 330. In the trend, control module variables can be displayed, however not all, but only those of the actual value, desired value and/or output variable type. One or more measurement data 335 can be assigned to each of these control module variables 330. The user viewpoint shows a currently valid configuration of a unit 320. A control module can have a plurality of variables depending upon the type. However only one measurement data item/measured value can be assigned to each variable.

From a historical batch data viewpoint 340 the measurement data are stored by means of the batch processes of each unit 320 in the batch 345 (measurement data storage 370). In this case a start and stop time 350 is assigned to each batch 345. The batch start time corresponds to the start of recording and simultaneously to the associated start of the biological/chemical process on the unit. The batch stop time corresponds to a corresponding end of the biological/chemical processes and simultaneously to the end of recording. The control modules 325 which are configured during the batch start and the control module variables 330 thereof as well as the measurement data 335 accrued during the process are also stored correspondingly in the batch 345. Thus each batch 345 stores a snapshot of the currently valid configuration as well as all measurement data or process data.

This has the advantage that completed/historical batches together with the currently valid configuration thereof can be considered or analyzed in the analysis area. At the same time, by means of the administration the computer system 160 enables an already new/different/modified configuration (novel or modified devices on the unit, renamed unit, modified control module name, deleted unit) of the respective equipment or devices 205, 210, 215. The user or monitoring viewpoint enables monitoring of the measurement data or process data with respect to a unit 320. The historical batch data viewpoint enables archiving of the measurement data and/or analysis, in particular offline analysis thereof. The communication viewpoint enables display of a measurement data flow as well as assignment of the measurement data.

The batches 345 and the associated process data can be stored in a database. This data can be exported as CSV (comma separated values) files from the SQL database for use in other tools. An efficient data compression can preferably be implemented in the database. This has the advantage that the stored measurement data can be output at high speed and in short time intervals in response to a corresponding database retrieval.

For example, a measurement data item can be composed of the following variables:

MappingShortID→Identification of control module variables;

Timestamp→time stamp: When is the measurement data item received in the unit 320. The time stamp can be issued centrally by the computer system 160 for each measurement data item, in order to achieve optimal precision;

Value→measured value of the measurement data item;

Quality→binary value, for example 0 for "good," 1 for "bad;" the quality can be determinative for whether the measurement data item is displayed by means of the display unit 100;

Checksum→Is generated by the computer system 160, in order to prevent data manipulation. This has the advantage that the security in the computer system 160 is increased.

For example, a detection unit 150 (as described above with respect to FIG. 1) in the computer system 160 can display the temporal correlation, as two units 135 A-N are combined into a group 400 (unit grouping).

Figure 4:
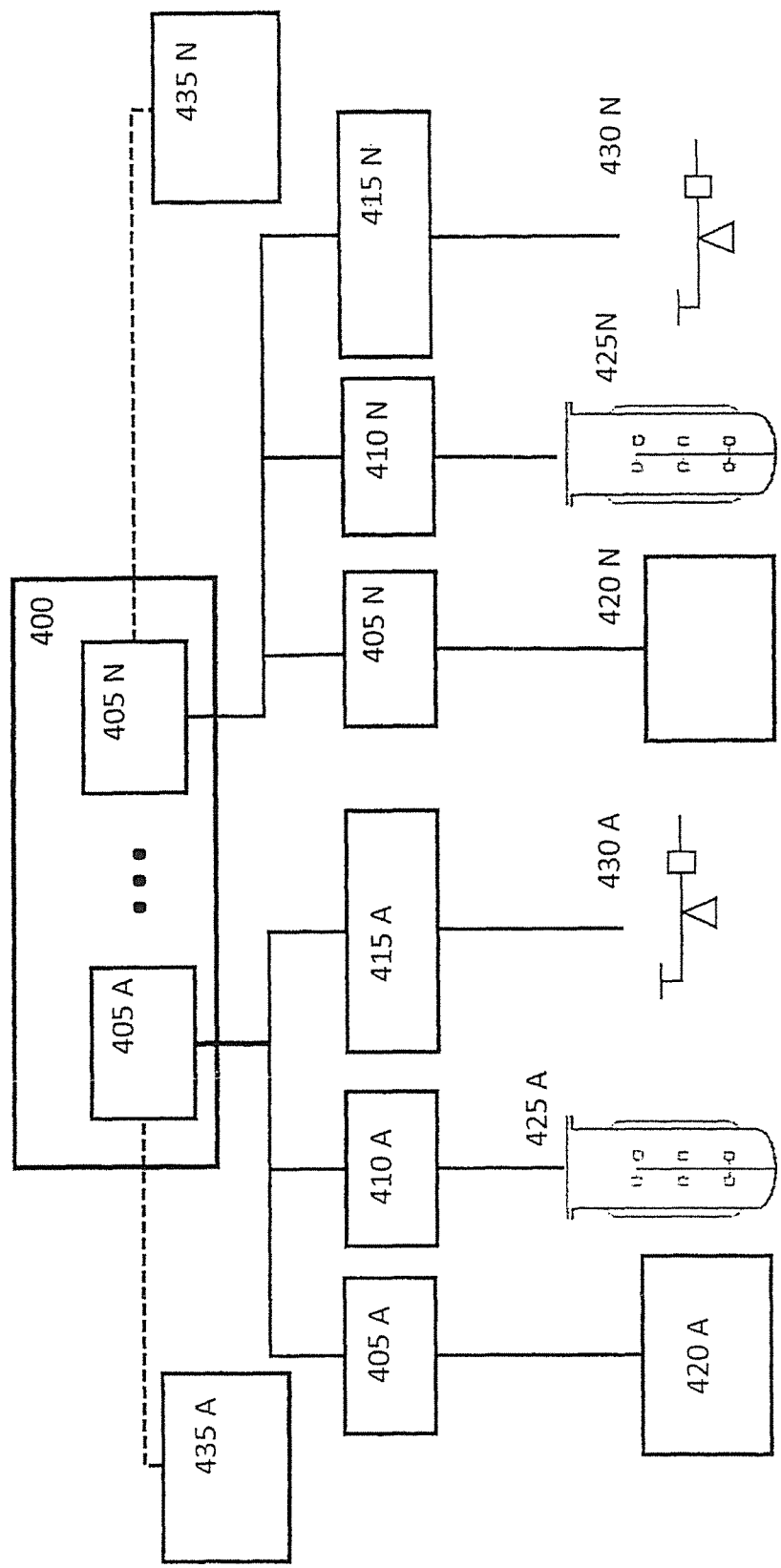
FIG. 4 shows a schematic representation of two units which are combined into a group.

FIG. 4 shows an example of a group 400 of at least two units 405 A-N. In the case of a grouping it is irrelevant whether the units 405 A-N are of the same type or have the same sensors 420 A-N or individual control units 430A-N.

Thus the system enables a free unit grouping combination, of which the detection unit 150 can display the temporal correlation. In this case the connection of the respective components to the respective units 405 A-N takes place in a similar manner to the connection as described above with respect to FIG. 2, i.e. the sensors 420 A-N are connected with the aid of a respective sensor device 406 A-N to the respective unit 405 A-N. The reactors 410 A-N can be coupled with the aid of corresponding reactor devices 410 A-N to the respective unit 405 A-N. The individual control units 430 A-N can be coupled with the aid of corresponding individual control devices 415 A-N to the respective unit 405 A-N. The respective individual control units 435 A-N can optionally be coupled to the respective units 405 A-N.

In this case the measurement data of the respective batches can be output with the aid of the display unit 100 either in a common display area or optionally in respective dedicated display areas by means of the display unit 100. In the case where the computer system 160 comprises three or more units 405 A-N, a group 400 can be formed which consists of an arbitrarily selectable combination of the units 405 A-N, which are to be temporally correlated. Moreover, it is possible that, with the aid of a respective display unit 100, different users can individually produce an arbitrary group 400, so that an individual temporal correlation of the measurement data corresponding to the group 400 can be initiated or carried out. Moreover, a snapshot of the measurement data which is displayed with corresponding time correlation by means of the display unit 100 can be produced and stored by each user by input of a corresponding command, for example by means of activation of a "report" button, so that said user can access the temporally correlated data at any time. While processes are running, each group 400 can also be broken up again automatically or manually by the user, for example when a specific, i.e. predetermined or predeterminable, condition is met.

In the case of unit grouping, by means of the respective process of the reactor and/or filter and also optionally the respective additional individual control units and internal individual control units, measurement data of the respective sensor is combined into a respective discrete batch and is displayed by means of the display unit 100.

Since above a specific density of data or data sets it is not possible for all data combined in a batch to be displayed simultaneously by means of the display unit 100, the computer system 160 can comprise a default according to which the display unit 100 always displays the last, most recent N data or data sets which have been detected and added to the batch, wherein N defines a specific, i.e. predetermined or predeterminable, number of data or data sets.

The temporal correlation can be displayed, as a time window of specific, i.e. predetermined or predeterminable, size is applied to the measurement data of the respective units 405 A-N in such a way that measurement data located in the time window are displayed with temporal correlation independently of an absolute time of detection thereof. In this case this temporal correlation or synchronization of the measurement data can be retained in the display unit 100, even if new measurement data is incorporated in the batch. The display unit 100 can display the temporal correlation of the data located within the time window. In particular, the synchronization may be a special type of temporal correlation, since measurement data which is displayed in a display area or display window is changed in terms of its size, in particular compressed or expanded, in relation to measurement data which is displayed in a second display area or display window.

This has the advantage that measurement data which has been detected and temporally correlated by the sensors of the two units is displayed independently of the absolute time of detection thereof via the time window. In this case the new data or data sets, which are detected by the sensors and are added to the corresponding batch, are not displayed by the display unit 100.

In another example the temporal correlation can be displayed, as measurement data which have been measured by sensors of the respective units 405 A-N at different time intervals, are brought into temporal correlation with one another. In particular, the size of the time window which is applied to the respective batch can be adapted in such a way that the measurement data correspond to one another in their time intervals. The temporal correlation can optionally be set manually by a user.

Figure 5:
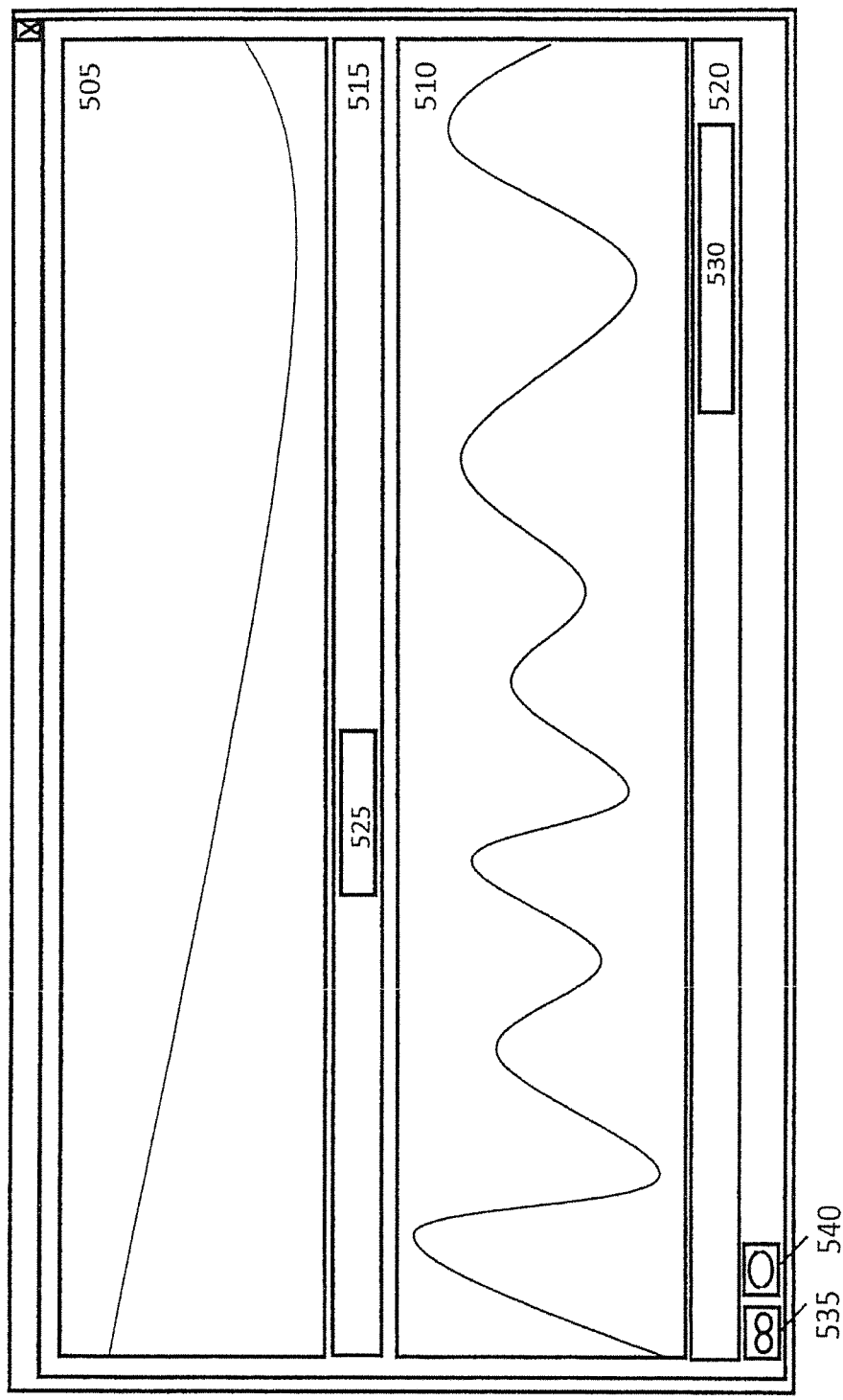
FIG. 5 shows an example of a display relating to measurement data output by means of the display unit.

FIG. 5 shows an example of a simplified illustrated display on a display unit 500, in which in the upper display area 505 a first zoom control 525 is provided which can be by means of a first zoombar 515. In this way a time window can be applied to the measurement data 335 of a first batch, also referred to below as a trend. Since the first zoom control 525 does not abut the right edge, the upper trend shows the measurement data of the batch from the selected time window, independently of an absolute time of detection of the measurement data 335. In the second display area 510 measurement data 335 of another unit is displayed, wherein a second zoom control 530 can be moved by means of a second zoombar 520. In this case a synchronization of the measurement data of both units is not possible, since the entire time period of the two trends is too different.

A user can control a breadth of the time window, i.e. a number of measurement data items 335 to be displayed, by controlling a point on the zoombar 515, 520, which is located outside the thumb, with the aid of a suitable input device. Thus the end of the thumb located on the side of the controlled point is expanded towards the point.

In particular, with the aid of a suitable input device the user can increase or decrease the width of the thumb as well as moving the thumb arbitrarily to the right and left within the zoombar 515, 520.

Figure 6:
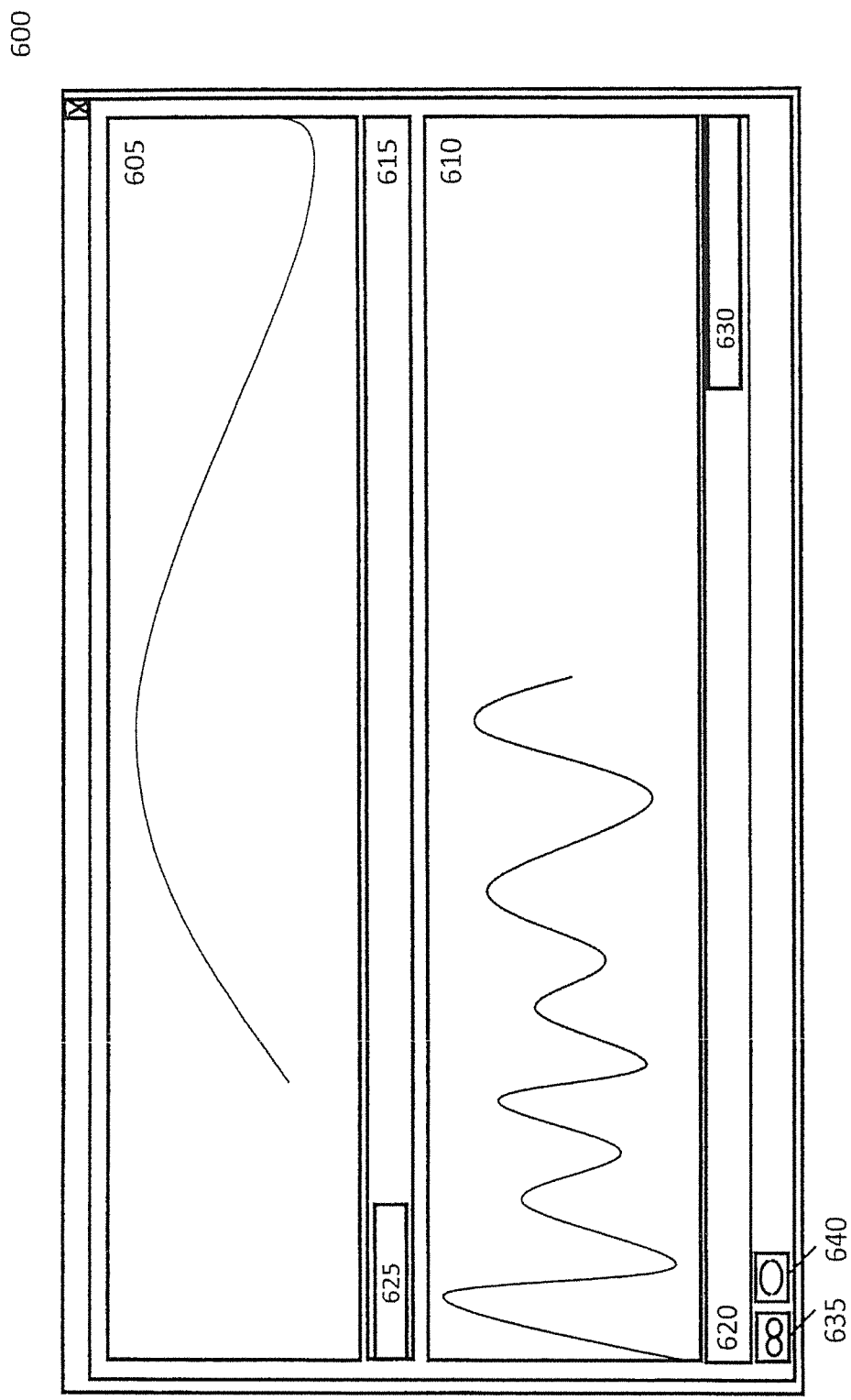
FIG. 6 shows an example of an arrangement of two thumbs.

FIG. 6 shows an example of an action which is only sometimes possible. In particular, FIG. 6 shows a first measurement data flow or trend by means of the display unit 600 in a first display area 605. The zoom control 625 is located at the extreme left in the zoombar 615. This may mean, for example, that the first measurement data 335 of the corresponding batch 345 is displayed. A second measurement data flow is displayed in a second display area 610, wherein the zoom control 630 is located at the extreme right of the corresponding zoombar 620. The two trends can be linked to one another with the aid of a corresponding button 635. In this case it is possible to carry out an action which includes a reduction in size of the area through a reduction in size of the respective zoom control 625, 630. However, a movement of the lower zoom control 630 (actuator) towards the left would not be possible, since the upper zoom control 625 (reactor) already abuts the left edge of the second zoombar 610. An example of implementation of this functionality is described below with reference to FIG. 10.

Figure 7:
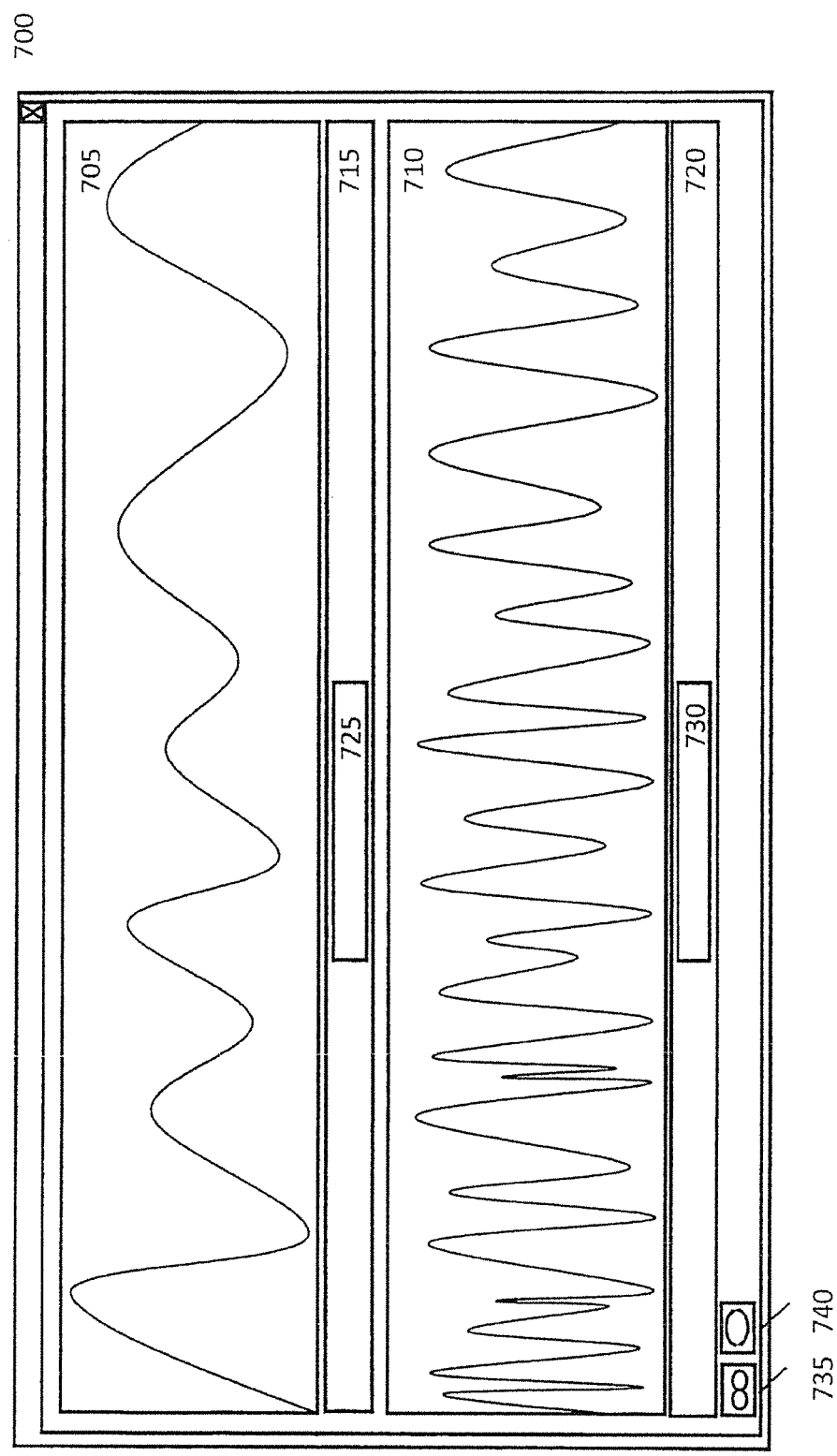
FIG. 7 shows an example of a display of measurement data before synchronization.
Figure 8:
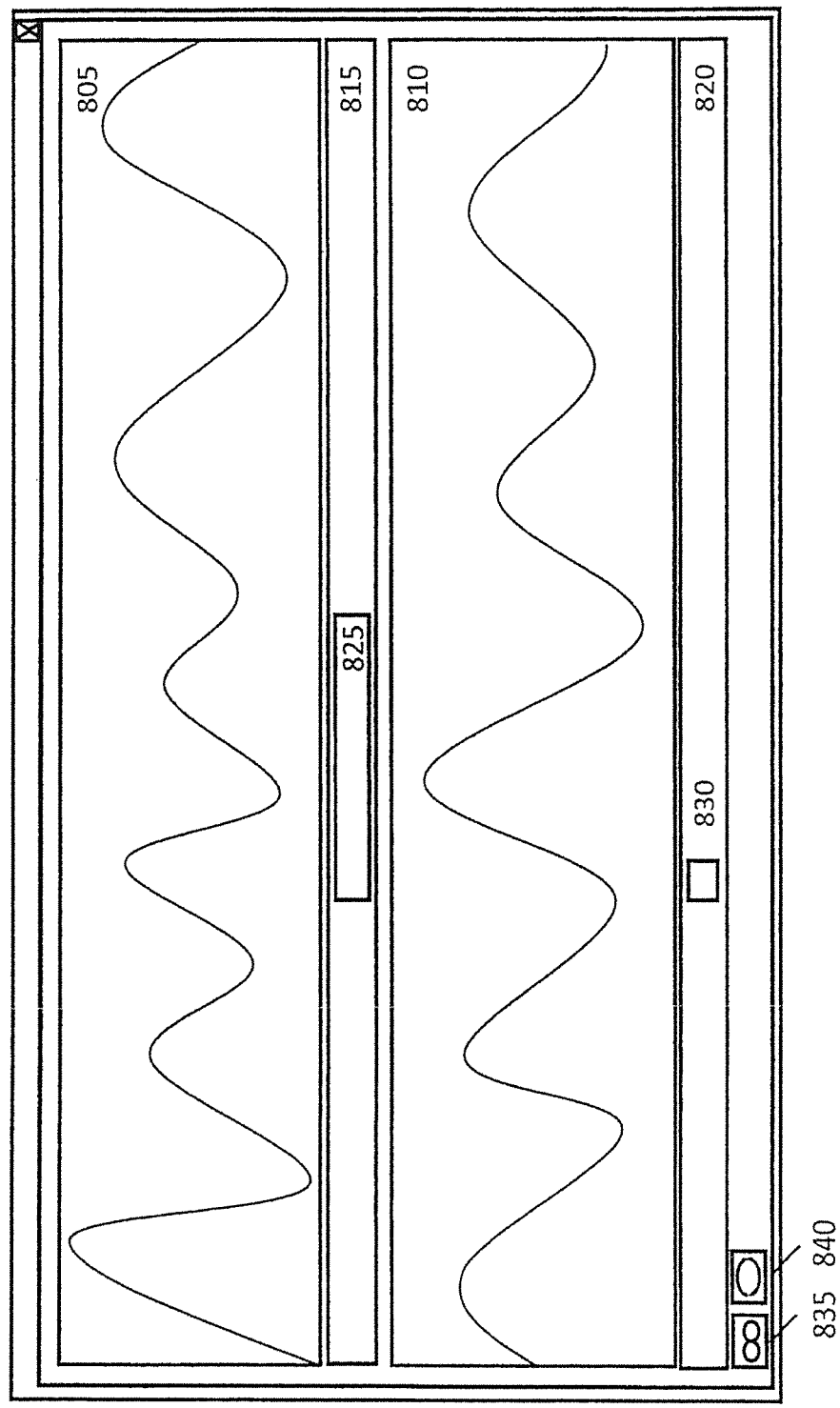
FIG. 8 shows the display of measurement data as in FIG. 7 after the synchronization.

FIG. 7 shows two measurement data flows respectively, in which a synchronization of the time axis is possible, wherein FIG. 8 shows the result of the synchronization of the time axes.

In particular, FIG. 7 shows a display unit 700, which displays a first measurement data flow of a first unit 135 A-N, 200, 320 in a first display area 705 as well as a second measurement data flow of a second unit 135 A-N, 200, 320 in a second display area 710. The respective zoom controls 725, 730 are the same size and are located in the same area of the particular zoombar 715, 720.

The two measurement data flows can be synchronized by activation of a corresponding button 740. The technical implementation explained below with reference to FIG. 9.

FIG. 8 shows the two measurement data flows as in FIG. 7, after the synchronization on the basis of an activation of the button 740 (FIG. 7) was activated. In particular, the fluctuations or changes of the respective measurement data in the respective display areas 805, 810 are now displayed synchronously relative to one another, i.e. at identical or similar intervals. In this case the relatively large size of the zoom control of the second display unit 830 has decreased, so that less measurement data is displayed in the corresponding display area 810, in order to enable the synchronized display of the measurement data. In this case, it is a question of which batch has already been running longer. Thus it is definitely possible that the lower or the upper trend or the zoombar thereof is reduced in size.

Figure 9:
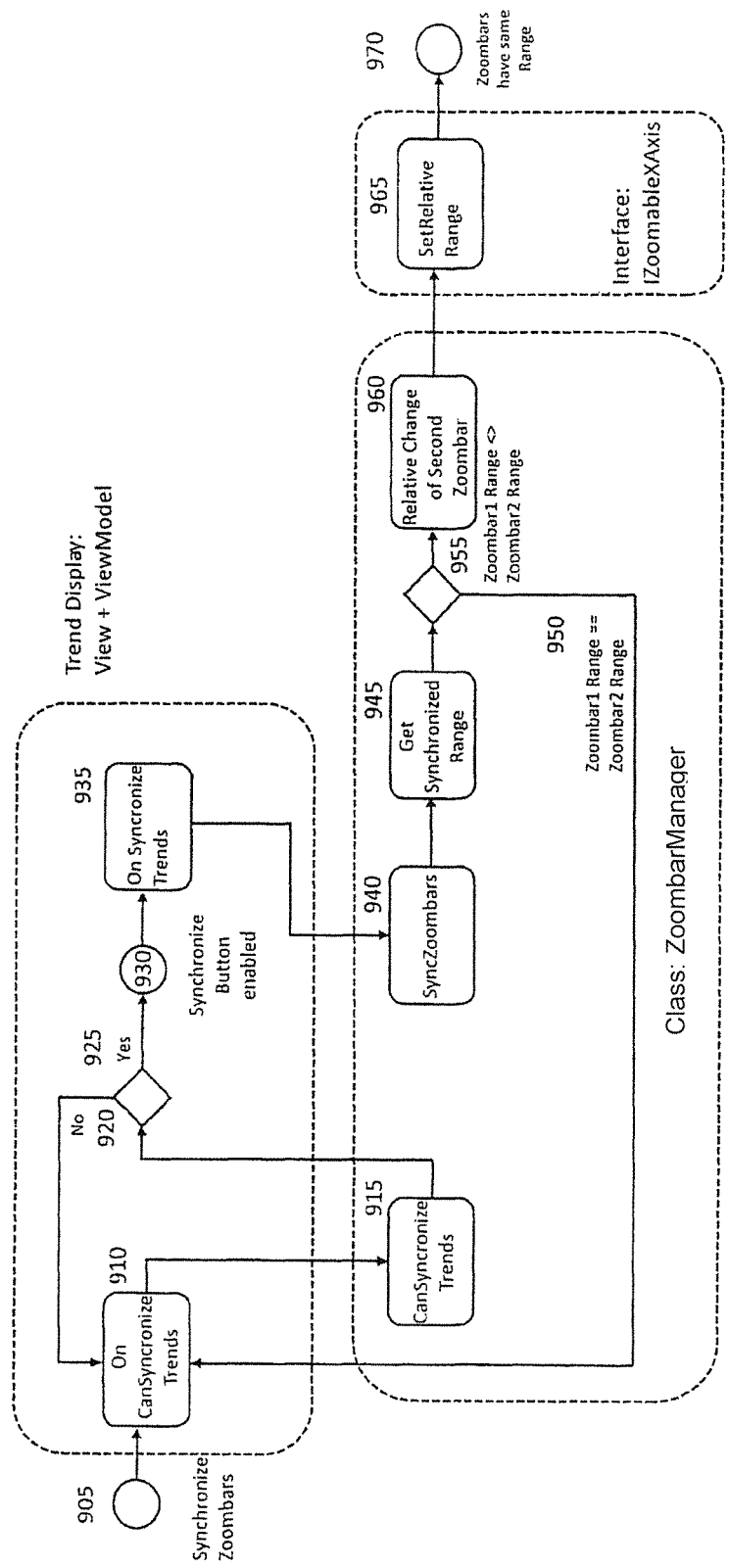
FIG. 9 shows a process flow diagram for synchronization.

FIG. 9 shows a process flow diagram, which visualizes a process of synchronization of the zoombar 715, 720, 815, 820, as explained above with respect to FIGS. 7 and 8. The process is explained in greater detail with the aid of an example of implementation of the respective method. First of all, a user can start 905 (Synchronize Zoombars) the synchronization of two zoombars 715, 720, 815, 820 with the aid of a corresponding activation, for example by activation of the button 740 in FIG. 7 or 840 in FIG. 8, also referred to below as the "synchronize" button. For example, the "synchronize" button can be linked in a WPF (Windows Presentation Foundation) via "Binding" and a command "SynchTrendsCommand," as can be seen from the following example of implementation:

```
<Button x:Name="SynchronizeTrendsButton"
                        Width="40"
                        Height="39"
                        Command="{TemplateBinding
SyncTrendsCommand}"
                        Style="{DynamicResource SAF_Toolbar_Button}"
                        self:FocusAttachments.SetFocusable="True"
                        IsTabStop="True"
                        ToolTip="{Binding           Source={x:Static
resources:Resource.SynchronizeTrendButtonToolTip}}">
                        <ContentControl Margin="0,0,0,1"
                                        Content="ContentControl"
                                        Focusable="False"
                                        IsTabStop="False"
                                        Style="{DynamicResource
02_012_24_24_Sync}" />
            </Button>
```

A command "SynchTrendsCommand" can be implemented in a class "TrendDisplay," i.e. a Model View ViewModel (MVVM) of the trend. MVVM is a variant of the Model View Controller pattern (MVC), which serves for separation of a display and logic of a user interface (UI), and is supported by the UI platform WPF.

An implementation of the command can take place with the aid of two methods, "OnSynchronizeTrends" 935 and/or "OnCanSynchronizeTrends" 910. In particular, the method OnSynchronizeTrends 935 in the class "TrendDisplay" can access the synchronization. On the other hand, the method "OnCanSynchronizeTrends" 910 can check whether a synchronization is possible. Accordingly, the "Synchronized" button can be activated/enabled or deactivated/disabled:

```
private void InitializeCommands( )
    {
        this.ExpandZoombarCommand = new
SAFCommand(this.OnExpandToMax, this.CanExpandToMax);
        this.SyncTrendsCommand = new
SAFCommand(this.OnSynchronizeTrends, this.OnCanSyncronizeTrends);
        this.LoadTemplateCommand = new
SAFCommand(this.OnLoadTemplate, this.CanLoadTemplate);
    }
```

The method OnSynchronizeTrends 910 can in turn access an internal method "SyncZoombars" 940 of the class "ZoombarManager" with both zoombars as transfer parameter:

```
private void OnSynchronizeTrends(object obj)
        {
             this.zoombarManager.SyncZoombars(this.-
trendControl1.ZoomBar, this.trendControl2.ZoomBar);
        }
```

Likewise the method "OnCanSynchronizeTrends" can internally access a method "CanSyncZoombars" (not illustrated in FIG. 9) from the class "ZoombarManager" with both zoombars as transfer parameter:

```
private bool OnCanSyncronizeTrends(object obj)
    {
        return
this.zoombarManager.CanSyncZoombars(this.trendControl1.ZoomBar,
this.trendControl2.ZoomBar);
    }
```

An example of an implementation of a determination of whether two zoombars can be synchronized is explained below:

In particular, this determination can be implemented as a method "CanSyncZoombars" internally accesses the method "GetSynchronizedRanges," which also transfers both zoombars as transfer parameter. In this case in particular a tuple of an X-axis or of a timeline of a batch and a zoom bar range can be transferred as a return value. If this return value is "zero," a synchronization is not possible, and the button remains deactivated or disabled. If the return value contains a tuple of correspondingly valid properties (X-axis and zoombar range), a check is carried out as to whether the minimum range of the zoombar to be changed is smaller than the range to be set. If that is the case, the Synchronize button is activated:

```
public bool CanSyncZoombars(IZoomableXAxis zoomableXAxis1,
IZoomableXAxis zoomableXAxis2)
    {
        var result = true;
        Tuple<IZoomableXAxis,    ZoombarRange>
zoombarAndRange          =
GetSyncronizedRanges(zoomableXAxis1, zoomableXAxis2);
        if (zoombarAndRange != null)
        {
            IZoomableXAxis zoombarToChange =
            zoombarAndRange.Item1;
            ZoombarRange rangeToSet = zoombarAndRange.Item2;
            if (zoombarToChange.MinimalThumbRange >
rangeToSet.Maximum – rangeToSet.Minimum) result = false;
        }
        else result = false;
        return result;
    }
```

The method SyncZoombars 940 can in turn internally access the method "GetSynchronizedRanges" 945 with both zoombars as transfer parameter. In this case a flag "inSyncAction" can be set in advance, in order to block other processes or actions in the meantime. Again a tuple (X-axis and zoombar range) can be a return value of the method. If the value is "zero," no action follows. If the tuple contains in each case valid objects, the range of the zoombar to be adapted is set (relatively) with the supplied values (SetRelativeRange 965; see FIG. 9), i.e. Range Minimum and Range Maximum:

```
public void SyncZoombars(IZoomableXAxis zoomableXAxis1,
IZoomableXAxis zoomableXAxis2)
    {
        inSyncAction = true;
        Tuple<IZoomableXAxis,    ZoombarRange>
        zoombarAndRange       =
GetSyncronizedRanges(zoomableXAxis1, zoomableXAxis2);
        if (zoombarAndRange != null)
        {
            IZoomableXAxis zoombarToChange =
            zoombarAndRange.Item1;
            ZoombarRange rangeToSet = zoombarAndRange.Item2;
            zoombarToChange.SetRelativeRange(rangeToSet.-
Minimum, rangeToSet.Maximum);
        }
        inSyncAction = false;
    }
```

In this case the relative range relates to the trend, independently of the absolute time thereof. In this connection a method "GetSynchronizedRanges" can be implemented, which accesses the ranges from the transferred X-axes:

zoombarRange
    zoombar1Range=zoomableXAxis1.GetRange( );

zoombarRange
    zoombar2Range=zoomableXAxis2.GetRange( );

Moreover, a calculation of an absolute time period. This has the advantage that zoombars which are not the same, are compared with the aid of the minimum or maximum of the corresponding ranges:

var zoombar1RangeSpan=(zoombar1Range.Maximum−
    zoombar1Range.Minimum)*
    (zoomableXAxis1.XAxisEnd−
    zoomableXAxis1.XAxisStart);

var zoombar2Rangespan=(zoombar2Range.Maximum−
    zoombar2Range.Minimum)*
    (zoomableXAxis2.XAxisEnd−
    zoomableXAxis2.XAxisStart);

In a subsequent step it is possible to compare which time period of the respective range is greater. Accordingly, the range to be adapted must be calculated differently:

Range.Minimum=zoombar2Range.Minimum

Range.Maximum=zoombar2Range.Minimum+RelativeChangeOfSecondZoombar
    (zoombar1Range.Maximum−
    zoombar1Range.Minimum,    zoomableXAxis1,
    zoomableXAxis2)

A Range.Maximum can be implemented with the aid of a method RelativeChangeOfSecondZoombar with the input parameters RelativeChangeOfZoombar, firstZoombar, secondZoombar:

```
private         Tuple<IZoomableXAxis,           ZoombarRange>
GetSyncronizedRanges(IZoomableXAxis       zoomableXAxis1,    IZoomableXAxis
zoomableXAxis2)
    {
        if (zoomableXAxis1 == null || zoomableXAxis2 == null) return null;
        ZoombarRange zoombar1Range = zoomableXAxis1.GetRange( );
        ZoombarRange zoombar2Range = zoomableXAxis2.GetRange( );
        var    zoombar1RangeSpan     =    (zoombar1Range.Maximum    −
zoombar1Range.Minimum)         *         (zoomableXAxis1.XAxisEnd         −
```

-continued

```
zoomableXAxis1.XAxisStart);
        var    zoombar2RangeSpan    =    (zoombar2Range.Maximum   –
zoombar2Range.Minimum)        *        (zoomableXAxis2.XAxisEnd   –
zoomableXAxis2.XAxisStart);
        if (Math.Round(zoombar1RangeSpan, 5) < Math.Round(zoombar2RangeSpan, 5))
        {
            if (zoombar1Range.Minimum < 1 – zoombar1Range.Maximum)
                return         new         Tuple<IZoomableXAxis,
ZoombarRange>(zoomableXAxis2,    new    ZoombarRange   {   Minimum   =
zoombar2Range.Minimum,    Maximum    =    zoombar2Range.Minimum   +
RelativeChangeOfSecondZoombar(zoombar1Range.Maximum               –
zoombar1Range.Minimum, zoomableXAxis1, zoomableXAxis2) });
            else       return       new       Tuple<IZoomableXAxis,
ZoombarRange>(zoomableXAxis2,    new    ZoombarRange   {   Minimum   =
zoombar2Range.Maximum                                             –
RelativeChangeOfSecondZoombar(zoombar1Range.Maximum               –
zoombar1Range.Minimum,    zoomableXAxis1,    zoomableXAxis2),   Maximum   =
zoombar2Range.Maximum });
        }
        else    if    (Math.Round(zoombar1RangeSpan,    5)    >
Math.Round(zoombar2RangeSpan, 5))
        {
            if (zoombar2Range.Minimum < 1 – zoombar2Range.Maximum)
                return         new         Tuple<IZoomableXAxis,
ZoombarRange>(zoomableXAxis1,    new    ZoombarRange   {   Minimum   =
zoombar1Range.Minimum,    Maximum    =    zoombar1Range.Minimum   +
RelativeChangeOfSecondZoombar(zoombar2Range.Maximum               –
zoombar2Range.Minimum, zoomableXAxis2, zoomableXAxis1) });
            else       return       new       Tuple<IZoomableXAxis,
ZoombarRange>(zoomableXAxis1,    new    ZoombarRange   {   Minimum   =
zoombar1Range.Maximum                                             –
RelativeChangeOfSecondZoombar(zoombar2Range.Maximum               –
zoombar2Range.Minimum,    zoomableXAxis2,    zoomableXAxis1),   Maximum   =
zoombar1Range.Maximum });
        }
        return null;
    }
```

With a method RelativeChangeOfSecondZoombar 960 (FIG. 9) the calculation of the Range.Maximum of the second zoombar can be implemented as follows:

```
RelativeChangeOfSecondZoombar =
relativeChangeOfFirstZoombar          *          (firstZoombar.XAxisEnd–
firstZoombar.XAxisStart)/(secondZoombar.XAxisEnd                 –
secondZoombar.XAxisStart);
    private       double       RelativeChangeOfSecondZoombar(double
relativeChangeOfFirstZoombar, IZoomableXAxis firstZoombar, IZoomableXAxis
secondZoombar)
    {
        return  relativeChangeOfFirstZoombar   *   (firstZoombar.XAxisEnd   –
firstZoombar.XAxisStart)     /     (secondZoombar.XAxisEnd        –
secondZoombar.XAxisStart);
    }
```

Figure 10:
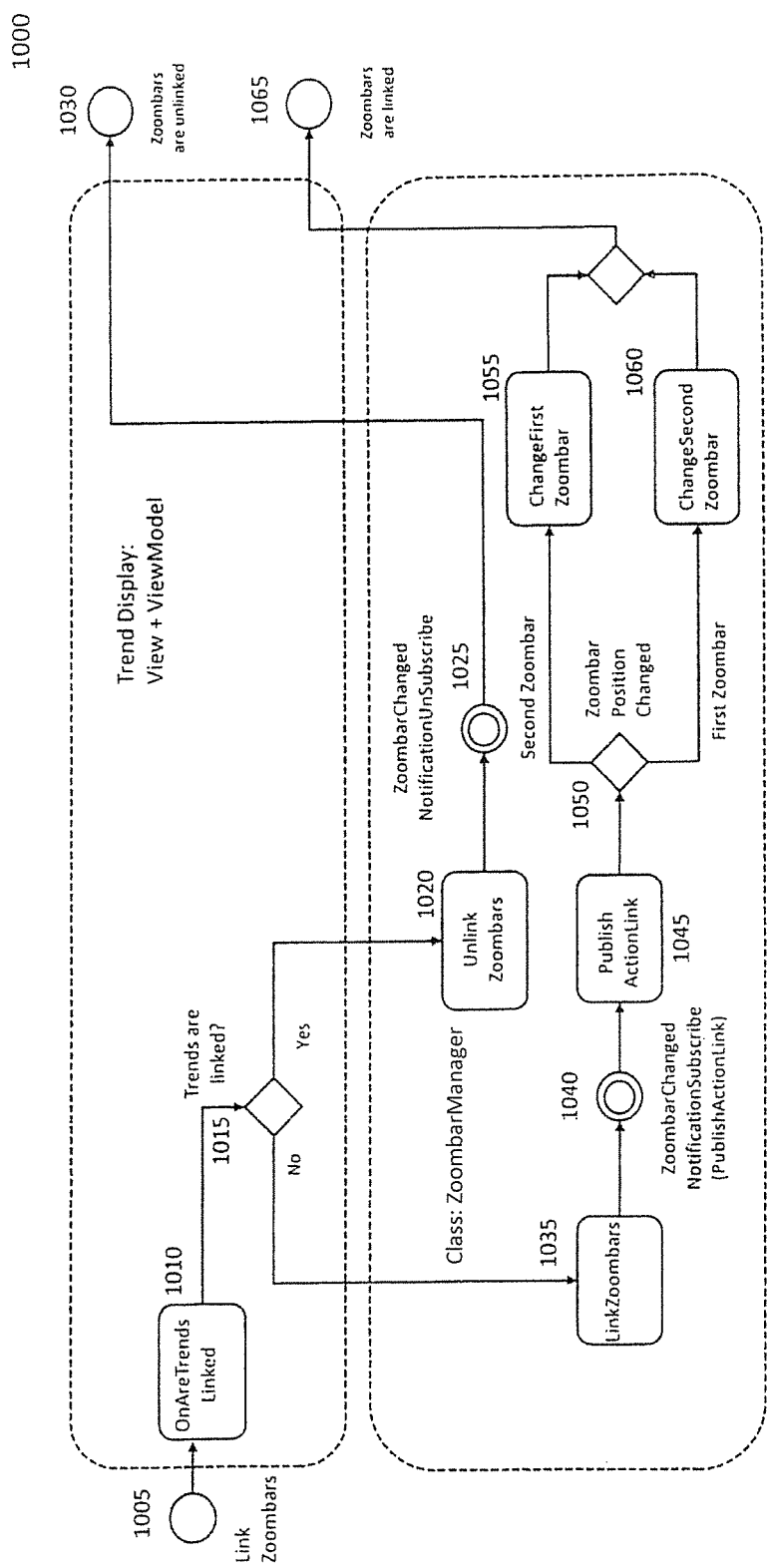
FIG. 10 shows a process flow diagram, which visualizes the process of linking the zoombars, as described with respect to FIGS. 7 and 8.

FIG. 10 shows a process flow diagram which visualizes a process of linking the zoombars 715, 720, 815, 820, as explained above with respect to FIGS. 7 and 8. The process is explained in greater detail with the aid of an example of implementation of the respective method. First of all, a user can start 1005 (Link Zoombars) the linking or unlinking of two zoombars 715, 720, 815, 820 with the aid of a corresponding activation, for example by activation of the button 735 in FIG. 7 or 835 in FIG. 8, also referred to below as the "LinkTrendsToggle" button. For example, the "LinkTrendsToggle" button can be bound by binding to a Boolean property "AreTrendsLinked," as can be seen from the following example of implementation:

```
<ToggleButton x:Name="LinkTrendsToggleButton"
        Width="40"
```

-continued

```
        Height="39"
        IsChecked="{Binding AreTrendsLinked,
                    RelativeSource={RelativeSource
                        TemplatedParent}}"
        Style="{DynamicResource TrendDisplay_LinkButtonStyle}"
        self:FocusAttachments.SetFocusable="True"
        IsTabStop="True"
        ToolTip="{Binding IsChecked, RelativeSource={RelativeSource
                Self},
        Converter={converters:BoolToStringConverter False= {x:Static
        resources:Resource.UnLinkedButtonToolTip}, True= {x:Static
        resources:Resource.LinkedButtonToolTip}}}"
        />
public bool AreTrendsLinked
    {
        get
```

```
        {
            return (bool)Getvalue(AreTrendsLinkedProperty);
        }
        set
        {
            this.SetValue(AreTrendsLinkedProperty, value);
        }
    }.
```

In this case the Boolean property "AreTrendsLinked," which can ascertain whether the corresponding trends are already linked, can be linked to a DependencyProperty "AreTrendsLinkedProperty," which with corresponding activation of the "LinkTrendsToggle" button can access a method "OnAreTrendsLinked" 1010, as can be seen from the following example of implementation:

```
public static readonly DependencyProperty AreTrendsLinkedProperty =
DependencyProperty.Register(
        "AreTrendsLinked", typeof(bool), typeof(TrendDisplay), new
FrameworkPropertyMetadata(false, OnAreTrendsLinked));
private static void OnAreTrendsLinked(DependencyObject d,
DependencyPropertyChangedEventArgs e)
    {
        var areTrendsLinked = (bool)e.NewValue;
        var trendDisplay = d as TrendDisplay;
        if (trendDisplay == null)
        {
            return;
        }
        if (areTrendsLinked)
    {
trendDisplay.zoombarManager.LinkZoombars(trendDisplay.-
trendControl1.ZoomBar, trendDisplay.trendControl2.ZoomBar);
    }
    else
    {
        trendDisplay.zoombarManager.UnlinkZoombars( );
            if (trendDisplay.trendControl1.IsVisible)
            {
                (trendDisplay.trendControl1.ExpandZoombar-
ToMaxCommand as SAFCommand).RaiseCanExecuteChanged( );
            }
            if (trendDisplay.trendControl2.IsVisible)
            {
                (trendDisplay.trendControl2.ExpandZoombar-
ToMaxCommand as SAFCommand).RaiseCanExecuteChanged( );
            }
        }
    }.
```

If the trends are already linked. the method "OnAreTrendsLinked" can access the method "UnlinkZoombars" 1020. If the trends are not linked. the method "OnAreTrendsLinked" can accordingly access the method "UnlinkZoombars" 1035. In this case the Boolean state of the Boolean property "AreTrendsLinked" can be modified accordingly. This is followed by an example of implementation of the methods "LinkZoombars" and "UnlinkZoombars":

```
    public void LinkZoombars(IZoomableXAxis zoomableXAxis1,
IZoomableXAxis zoomableXAxis2)
    {
        if (trendsAreLinked == true) return;
        this.zoomables = new Dictionary<int, IZoomableXAxis>( );
        this.zoomables.Add(1, zoomableXAxis1);
        this.zoomables.Add(2, zoomableXAxis2);
        // if range of the one zoombar changes: call OnRangeChanged
on the other (and prevent further zoombarChangedNotification)
        this.linkSubscriptionToken =
this.zoombarChangedNotification.Subscribe(PublishActionLink);
        trendsAreLinked = true;
    }
    public void UnlinkZoombars( )
    {
        if(this.zoomables != null) this.zoomables.Clear( );
        if(linkSubscriptionToken != null)
this.zoombarChangedNotification.Unsubscribe(this.-
linkSubscriptionToken);
            this.linkSubscriptionToken = null;
            trendsAreLinked = true;
    }
```

When the method "LinkZoombars" 1035 is accessed, an event "OnZoombarChangedNotification" can be subscribed 1040 (ZoombarChangedNotificationSubscribe) and can be linked 1045 to a method "PublishActionLink" 1065 (Zoom bars are linked). The event "OnZoombarChangedNotification" and consequently the method "PublishActionLink" can be accessed with each movement of a zoom control along each zoombar. In the method "PublishActionLink" can the functionality that a user can control both time windows with the aid of one single zoom control is implemented. With the aid of this functionality the user can control both time windows by moving the zoom control by means of the zoombar of a unit (actuator) 1050 (ZoombarPositionChanged), so that the time window is correspondingly shifted. In this case the movement of the time window can be applied both to the measurement data of the actuator 1055 (ChangeFirstZoombar) and also to the measurement data of the second unit (reactor) 1060 (ChangeSecondZoombar), in so far as this is possible for both units (as described above with respect to FIG. 6). This is followed by an example of implementation of the method "PublishActionLink":

```
private void PublishActionLink(ZoombarRangeChangedNotificationArgs
args)
    {
        // if trends are not linked: nothing to do
        if (trendsAreLinked == true) return;
        // all range changed call the notification again, then: do nothing
        if (inLinkAction || inSyncAction || inExpandToMaxAction)
        return;
        inLinkAction = true;
        var otherZoomable = this.zoomables.First(z => z.Value ==
args.ZoomableXAxis);
        var key = otherZoomable.key;
        if (key == 1)
        {
            // correct the second zoombar
            this.OnRangeChanged(args.Args.NewRange,
args.Args.OldRange, this.zoomables[1], this.zoomables[2]);
        }
        else
        {
            // correct the first zoombar
            this.OnRangeChanged(args.Args.NewRange,
args.Args.OldRange, this.zoomables[1], this.zoomables[2]);
        }
        inLinkAction = false;
    }
```

When the method "UnlinkZoombars" 1020 is accessed, a subscription to the event "OnZoombarChangedNotification" can be terminated again 1025 (ZoombarChangedNotificationUnSubscribe), so that a movement of a time window no longer affects the other time window 1030 (zoom are unlinked).

Figure 11:
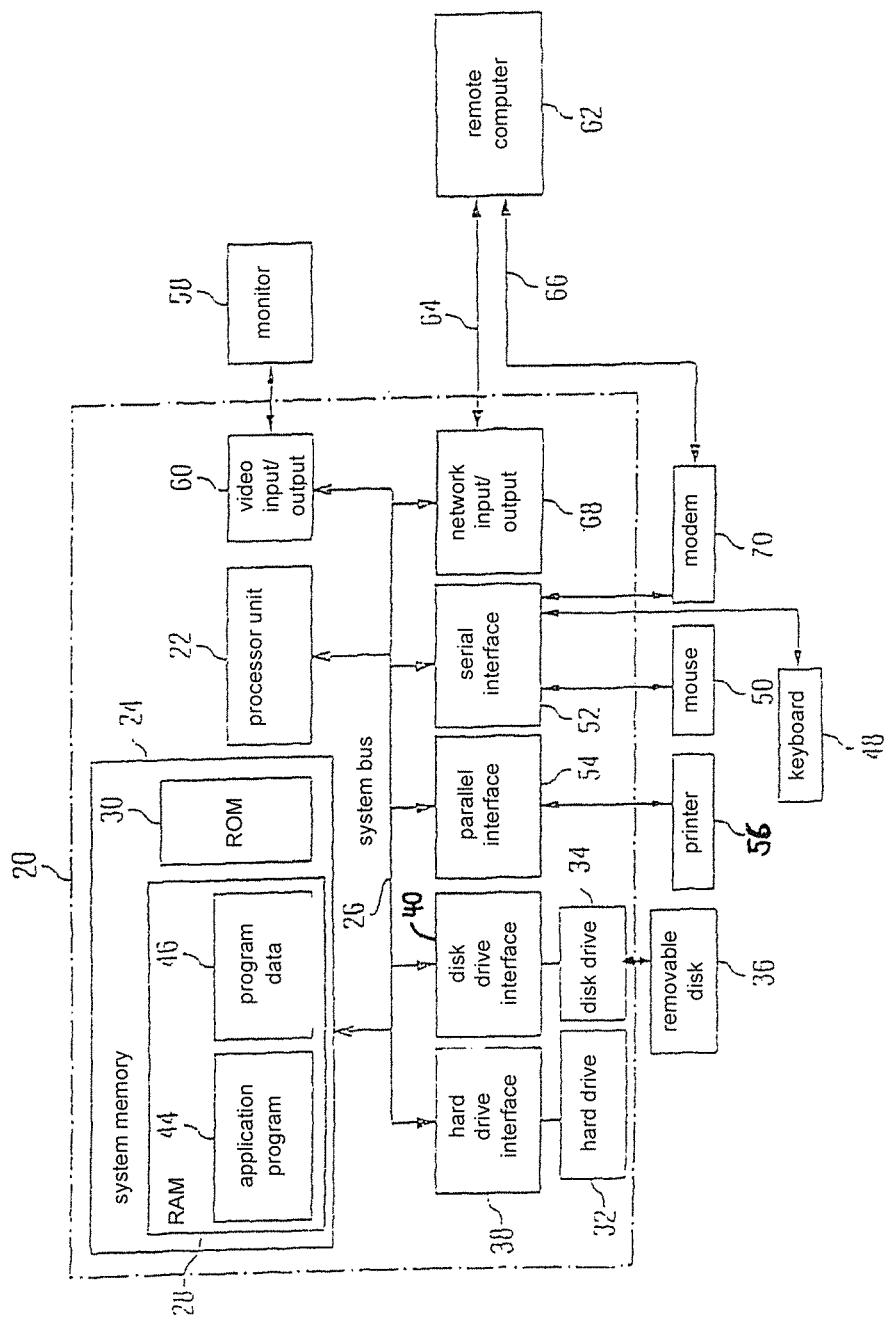
FIG. 11 shows an example of a system for implementation of the invention.

With reference to FIG. 11, an example of a system for implementing the invention is described. An example of a system comprises a universal computer unit in the form of a conventional computer environment 20 for example a "personal computer" (PC) 20, with a processor unit 22, a system memory 24 and a system bus 26, which connects a plurality of system components, inter alia the system memory 24 and the processor unit 22. The processor unit 22 can carry out arithmetic, logical and/or control operations, as the system memory 24 is accessed. The system memory 24 can store information and/or instructions for use in combination with the processor unit 22. The system memory 24 can include volatile and non-volatile memory, for example "random access memory" (RAM) 28 and "read-only memory" (ROM) 30. A basic input-output system (BIOS), which contains the basic routines which help to transfer information between the elements within the PCs 20, for example during the starting up, can be stored in the ROM 30. The system bus 26 may be one of many bus structures, inter alia a memory bus or a memory controller, a peripheral bus and a local bus, which uses one specific bus architecture from a plurality of bus architectures.

Furthermore, the PC 20 can have a hard drive 32 for reading or writing to a hard disk (not shown) and an external drive 34 for reading or writing to a removable disk 36 or a removable data storage medium. The removable disk may be a magnetic disk or a magnetic diskette for a magnetic disk drive or diskette drive or an optical diskette, such as for example a CD-ROM, for an optical disk drive. The hard drive 32 and the external disk drive 34 are respectively connected to the system bus 26 by means of a hard drive interface 38 and a disk drive interface 40. The drives and the associated computer-readable media provide a non-volatile memory for computer-readable instructions, data structures, program modules and other data for the PC 20. The data structures can have the relevant data for implementing a method as described above. Although the environment described by way of example uses a hard disk (not shown) and an external disk 42, for the person skilled in the art it is obvious that other types of computer-readable media which can store computer-accessible data can be used in the exemplary work environment, such as, for example, magnetic cassettes, flash memory cards, digital video diskettes, random access memories, read-only memories, etc.

A plurality of program modules, in particular an operating system (not shown), one or more application programs 44 or program modules (not shown) and program data 46, can be stored on the hard disk, the external disk 42, the ROM 30 or the RAM 28. The application programs can comprise at least a part of the functionality as shown in FIG. 1 or FIGS. 5 to 9.

A user can input commands and information, as described above, into the PC 20 with the aid of input devices such as, for example, a keyboard 48 and a computer mouse 50. Other input device (not shown) can comprise a microphone and other sensors, a joystick, a game pad, a scanner or the like. These or other input devices can be connected to the processor unit 22 with the aid of a serial interface 52 which is connected to the system bus 26 or can be connected with the aid of other interfaces such as, for example, a parallel interface 54, a game port or a universal serial bus (USB). Furthermore, information can be printed by a printer 56. The printer 56 and other parallel input/output devices can be connected to the processor unit 22 by the parallel interface 54. A monitor 58 or other types of display device(s) is/are connected to the system bus 26 by means of an interface such as, for example, a video input/output 160. In addition to the monitor, the computer environment 20 can comprise other peripheral output devices (not shown) such as, for example, loudspeakers or acoustic outputs.

The computer environment 20 can communicate with other electronic devices, for example a computer, a corded telephone, a cordless telephone, a personal digital assistant (PDA), a television or the like. In order to communicate, the computer environment 20 can operate in a networked environment, wherein connections to one or more electronic devices are used. FIG. 11 shows the computer environment networked with a remote computer 62. The remote computer 62 can be another computer environment, e.g., a server, a router, a network PC, an equivalent or peer device or other conventional network nodes, and can comprise many or all of the elements described above with regard to the computer environment 20. The logic connections, such as those shown in FIG. 11, comprise a local area network (LAN) 64 and a wide area network (WAN) 66. Such network environments are customary in offices, company-wide computer networks, intranets and the internet.

When a computer environment 20 is used in a LAN network environment, the computer environment 20 can be connected to the LAN 64 by a network input/output 68. If the computer environment 20 is used in a WAN network environment, the computer environment 20 can comprise a modem 70 or other means for producing communication via the WAN 66. The modem 70, which can be internal and external with respect to the computer environment 20, is connected to the system bus 26 by means of the serial interface 52. In the network environment, program modules which are shown relative to the computer environment 20, or sections thereof, can be stored in a remote memory device, which is accessible on or from a remote computer 62 or is part of the system. Furthermore, other data which are relevant for the method and/or system described above can be accessible on or from the remote computer 62.

LIST OF REFERENCE SIGNS 20 computer environment
22 processor unit
24 system memory
26 system bus
28 random access memory (RAM)
30 read-only memory (ROM)
32 hard drive
34 disk drive
36 removable disk
38 hard drive interface
40 disk drive interface
44 application program
46 program data
48 keyboard
50 computer mouse
52 serial interface
54 parallel interface
56 printer
58 monitor
60 video input/output
62 remote computer
64 local area network (LAN)
66 wide area network (WAN)
68 network input/output
70 modem
100 display unit
105 display area
110 display area
115 zoombar 120 zoombar
125 zoom control
130 zoom control
135A-N unit
140A-N sensor
145 network (LAN, WAN)
150 detection unit
155 control module
160 computer system for controlling, detecting, regulating and/or analyzing biological, biochemical, chemical and/or physical processes
200 unit
205 sensor device
210 reactor device
215 individual control unit device
220 sensor, for example $O_2/CO_2$ analyzer or analysis sensor
225 bioreactor
230 individual control unit, for example scale
235 internal individual control units
305 communication viewpoint
310 device
315 user/monitoring viewpoint
320 unit
325 control module
330 control module variable
335 measurement data
340 historical batch data viewpoint
345 batch
350 start and stop time
355 unit stored in batch
360 control module stored in batch
365 data set characteristic sensor
370 measurement data stored in batch
400 group
405A . . . N unit
406A . . . N sensor device
410A . . . N reactor device
415A . . . N individual control unit device
420A . . . N sensors
425A . . . N bioreactor
430A . . . N individual control unit
435A . . . N internal individual control units
500 exemplary display unit
505 first display area for display of measurement data
510 second display area for display of measurement data
515 first zoombar
520 second zoombar
525 first zoom control
530 second zoom control
535 linking button
540 synchronization button
600 exemplary display unit
605 first display area for display of measurement data
610 second display area for display of measurement data
615 first zoombar
620 second zoombar
625 first zoom control
630 second zoom control
635 linking button
640 synchronization button
700 exemplary display unit
705 first display area for display of measurement data
710 second display area for display of measurement data
715 first zoom bar
720 second zoombar
725 first zoom control
730 second zoom control
735 linking button
740 synchronization button
800 exemplary display unit
805 first display area for display of measurement data
810 second display area for display of measurement data
815 first zoom bar
820 second zoombar
825 first zoom control
830 second zoom control
835 linking button
840 synchronization button
905 synchronize zoom bars
910 OnCanSynchronize Trends
915 CanSynchronize Trends
920 CanNotSynchronize
925 CanSynchronize
930 Synchronize Button enabled
935 OnSynchronizeTrends
940 SyncZoom bars
945 GetSynchronizedRange
950 Ranges Fit
955 Ranges Do Not Fit
960 RelativeChange of Second Zoom bar
965 SetRelativeRange
970 Zoombars Have Same Range
1005 Unlink Zoombars
1010 OnAreTrendsLinked
1015 Trends are linked?
1020 Unlink Zoombars
1025 ZoombarChanged NotificationUnSubscribe
1030 Zoombars are unlinked
1035 Link Zoombars
1040 ZoombarChanged NotificationSubscribe
1045 Publish ActionLink
1050 Zoombar Position Changed
1055 ChangeFirstZoombar
1060 ChangeSecondZoombar
1065 Zoombars are linked

The invention claimed is:

1. A computer system (160) for controlling, detecting, regulating and/or analyzing biological, biochemical, chemical and/or physical processes, comprising:
at least two units (135 A-N, 200, 320, 405A-N) that are designed to receive a substance in order to carry out at least one biological, biochemical, chemical and/or physical process on said substance;
wherein each of the units (135 A-N, 200, 320, 405A-N) has at least one sensor (140A-N, 220, 420A-N) that is configured to detect measurement data (335) in the respective unit (135 A-N, 200, 320, 405A-N) relating to the process;
a detection unit (150) that is designed to automatically recognize a temporal correlation of the detected measurement data by comparing, in real time, a flow of measurement data (335) of the respective units (135 A-N, 200, 320, 405A-N) with one another, wherein the temporal correlation is based on a reaching, exceeding or undershooting of a selected limit value;
at least one display unit (100, 500, 600, 700, 800), by means of which the measurement data (335) of the at least two units (135 A-N, 200, 320, 405A-N) is displayed in the respective temporal correlation that allows information to be obtained on a relationship between the displayed measurement data (335) such that changes of one or more process factors in a first unit as compared to at least one second unit are detected; and at least one control module (155) that is designed to automatically adjust at least one parameter of at least one process carried out on said substance based on the detected changes of one or more process factors.

2. The computer system of claim 1, wherein the temporal correlation can be displayed, as a time window of specific size, is applied to the measurement data (335) of the respective units (135 A-N, 200, 320, 405A-N) in such a way that measurement data (335) located in the time window are displayed with temporal correlation independently of an absolute time of detection thereof.

3. The computer system of claim 1, wherein the measurement data (335) of the at least two units (135 A-N, 200, 320, 405A-N) is displayed by means of the display unit (100, 500, 600, 700, 800) in a respective display area (105, 110, 505, 510, 605, 610, 705, 710, 805, 810);
wherein, during the setting, in each display area (105, 110, 505, 510, 605, 610, 705, 710, 805, 810) the user applies a respective time window at a specific time to the measurement data (335) with the aid of a zoom control (825, 830) that can be moved along the measurement data (335) in the respective display area (105, 110, 505, 510, 605, 610, 705, 710, 805, 810).

4. The computer system of claim 1, wherein the control module (155) that is designed to combine at least two units (135 A-N, 200, 320, 405A-N) into a group.

5. The computer system of claim 4, wherein the control module (155) also is designed to link together time windows that are applied over measurement data (335) of the respective units (135 A-N, 200, 320, 405A-N) and that are displayed in a respective display area (105, 110, 505, 510, 605, 610, 705, 710, 805, 810), so that a user can control the time window with the aid of a zoom control (825, 830) by moving the time window synchronously over the measurement data (335) of the respective units (135 A-N, 200, 320, 405A-N).

6. The computer system of claim 4, wherein the control module (155) is designed so that, at the same time and independently of the absolute time, the control module (155) starts the process that is to be carried out on the substance of the respective units (135 A-N, 200, 320, 405A-N).

7. The computer system of claim 1, wherein the temporal correlation can be set as a function of a user input.

8. A computer-implemented method for controlling, detecting, regulating and/or analyzing biological, biochemical, chemical and/or physical processes, comprising:
providing at least two units (135 A-N, 200, 320, 405A-N) that are designed to receive a substance in order to carry out at least one biological, biochemical, chemical and/or physical process on said substance, wherein each of the units (135 A-N, 200, 320, 405A-N) has at least one sensor,
using the sensors for detecting measurement data (335) in the respective units (135 A-N, 200, 320, 405A-N) relating to the respective process,
recognizing a temporal correlation of the detected measurement data by a detection unit (150) by comparison, in real time, of a run of measurement data (335) of the respective units (135 A-N, 200, 320, 405A-N) with one another, wherein the temporal correlation is based on a reaching, exceeding or undershooting of a selected limit value;
displaying the measurement data (335) of the at least two units (135 A-N, 200, 320, 405A-N) according to the temporal correlation by a display unit (100, 500, 600, 700, 800) wherein the temporal correlation allows information to be obtained on a relationship inherent in the displayed measurement data (335) such that changes of one or more process factors in a first unit as compared to at least one second unit are detected; and
adjusting, by means of a control module (155), at least one parameter of at least one process carried out on said substance based on the detected changes of one or more process factors.

9. The method of claim 8, additionally comprising:
wherein the temporal correlation can be displayed, as a time window of specific size is applied to the measurement data (335) of the respective units (135 A-N, 200, 320, 405A-N) in such a way that measurement data (335) located in the time window are displayed with temporal correlation independently of an absolute time of detection thereof.

10. A non-transitory computer readable storage medium for storing a computer program product comprising program parts which, when executed in a computer, causes the computer to perform the computer-implemented method of claim 9.

11. The method of claim 8, further comprising:
setting the temporal correlation as a function of a user input;
displaying the measurement data (335) of the at least two units (135 A-N, 200, 320, 405A-N) by the display unit (100, 500, 600, 700, 800) in a respective display area (105, 110, 505, 510, 605, 610, 705, 710, 805, 810); and
during the setting, in each display area (105, 110, 505, 510, 605, 610, 705, 710, 805, 810) the user applies a respective time window at a specific time to the measurement data (335) with the aid of a zoom control (825, 830) that can be moved along the measurement data (335) in the respective display area (105, 110, 505, 510, 605, 610, 705, 710, 805, 810).

12. The method of claim 8, further comprising:
combining at least two units (135 A-N, 200, 320, 405A-N) to form a group, by means of the control module (155), so that the group can be controlled by means of the control module (155);
linking time windows that are applied over measurement data (335) of the respective units (135 A-N, 200, 320, 405A-N) displayed in a respective display area (105, 110, 505, 510, 605, 610, 705, 710, 805, 810) by means of the control module (155), so that a user can control the time window with the aid of a zoom control (825, 830) by moving the time window synchronously over the measurement data (335) of the respective units (135 A-N, 200, 320, 405A-N).

13. The method of claim 8 further comprising:
starting the processes that are to be carried out on the substances of the respective units (135 A-N, 200, 320, 405A-N), at the same time and independently of the absolute time, by means of the control module (155).

14. A graphical user interface for controlling, detecting, regulating and/or analyzing biological, biochemical, chemical and/or physical processes, comprising:
at least two display areas (105, 110, 505, 510, 605, 610, 705, 710, 805, 810) of specific size and specific position, wherein each display area (105, 110, 505, 510, 605, 610, 705, 710, 805, 810) is coupled to at least one control module (155) and a unit (135 A-N, 200, 320, 405A-N) that is designed to receive a substance in order to carry out at least one biological, biochemical, chemical and/or physical process on said substance,
wherein each of the units (135 A-N, 200, 320, 405A-N) has at least one sensor that is configured to detect measurement data (335) in the respective unit (135 A-N, 200, 320, 405A-N) about the process, a detection unit (150) that is designed to automatically recognize a temporal correlation of the detected measurement data by comparing, in real time, a flow of measurement data (335) of the respective units (135 A-N, 200, 320, 405A-N) with one another, wherein the temporal correlation is based on a reaching, exceeding or undershooting of a selected limit value;

wherein in each display area (105, 110, 505, 510, 605, 610, 705, 710, 805, 810) the measurement data (335) of the at least two units (135 A-N, 200, 320, 405A-N) is displayed in the respective temporal correlation based on the at least one condition and independently of an absolute time of detection thereof, the temporal correlation allows information to be obtained on a relationship inherent in the displayed measurement data (335) such that changes of one or more process factors in a first unit as compared to at least one second unit are detected, and wherein the at least one control module (155) is designed to automatically adjust at least one parameter of at least one process carried out on said substance based on the detected changes of one or more process factors.

15. The graphical user interface of claim 14, wherein the temporal correlation can be set as a function of a user input.

* * * * *